(12) United States Patent
Kitching et al.

(10) Patent No.: US 10,342,638 B2
(45) Date of Patent: Jul. 9, 2019

(54) TREATMENT PLANNING AND PROGRESS TRACKING SYSTEMS AND METHODS

(75) Inventors: Ian Kitching, Saratoga, CA (US); Rene Sterental, Palto Alto, CA (US); Eric Kuo, Foster City, CA (US); Lou Shuman, Chevy Chase, MD (US)

(73) Assignee: Align Technology, Inc., San Jose, CA (US)

( * ) Notice: Subject to any disclaimer, the term of this patent is extended or adjusted under 35 U.S.C. 154(b) by 1510 days.

(21) Appl. No.: 12/129,578

(22) Filed: May 29, 2008

(65) Prior Publication Data

US 2008/0305454 A1 Dec. 11, 2008

Related U.S. Application Data

(63) Continuation-in-part of application No. 11/760,701, filed on Jun. 8, 2007, now abandoned.

(51) Int. Cl.
*A61C 7/00* (2006.01)

(52) U.S. Cl.
CPC ................ *A61C 7/00* (2013.01); *A61C 7/002* (2013.01)

(58) Field of Classification Search
USPC ............................................ 705/2, 3; 433/24
See application file for complete search history.

(56) References Cited

U.S. PATENT DOCUMENTS

| 2,467,432 | A | 4/1949 | Kesling |
| 3,407,500 | A | 10/1968 | Kesling |
| 3,600,808 | A | 8/1971 | Reeve |
| 3,660,900 | A | 5/1972 | Andrews |
| 3,683,502 | A | 8/1972 | Wallshein |
| 3,738,005 | A | 6/1973 | Cohen |
| 3,860,803 | A | 1/1975 | Levine |
| 3,916,526 | A | 11/1975 | Schudy |
| 3,922,786 | A | 12/1975 | Lavin |
| 3,950,851 | A | 4/1976 | Bergersen |
| 3,983,628 | A | 10/1976 | Acevedo |
| 4,014,096 | A | 3/1977 | Dellinger |
| 4,195,046 | A | 3/1980 | Kesling |

(Continued)

FOREIGN PATENT DOCUMENTS

| AU | 3031677 | 5/1979 |
| AU | 517102 | 7/1981 |

(Continued)

OTHER PUBLICATIONS

Alcaniz, et al., "An Advanced System for the Simulation and Planning of Orthodontic Treatments," Karl Heinz Hohne and Ron Kikinis (eds.), *Visualization in Biomedical Computing, 4th Int'l. Conf., VBC '96*, Hamburg, Germany, Sep. 22-25, 1996, Springer-Verlag, pp. 511-520.

(Continued)

*Primary Examiner* — Lena Najarian
(74) *Attorney, Agent, or Firm* — Wilson Sonsini Goodrich & Rosati

(57) ABSTRACT

The present invention provides systems and methods of managing planning and delivery of an orthodontic treatment using planning tools, treatment guidelines, instructions and appointment planning tools customized to the individual patient being treated, as well as tools and methods for tracking delivery and patient progression through an orthodontic treatment plan.

13 Claims, 18 Drawing Sheets

(56) References Cited

U.S. PATENT DOCUMENTS

| | | |
|---|---|---|
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,752,832 A * | 5/1998 | Vardimon ............... A61C 19/04 33/514 |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,067,523 A | 5/2000 | Bair et al. |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 * | 11/2001 | Sachdeva et al. ............... 433/24 |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,406,292 B1 | 6/2002 | Chishti et al. |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,074,038 B1 | 7/2006 | Miller |
| 7,077,647 B2 | 7/2006 | Choi et al. |
| 7,156,661 B2 | 1/2007 | Choi et al. |
| 7,357,636 B2 | 4/2008 | Hedge et al. |
| 7,474,307 B2 | 1/2009 | Chishti et al. |
| 8,075,306 B2 | 12/2011 | Kitching et al. |
| 8,562,338 B2 | 10/2013 | Kitching et al. |
| 8,636,510 B2 | 1/2014 | Kitching et al. |
| 8,899,978 B2 | 12/2014 | Kitching et al. |
| 9,017,072 B2 | 4/2015 | Kitching et al. |
| 9,060,829 B2 | 6/2015 | Sterental et al. |

(56) References Cited

U.S. PATENT DOCUMENTS

| | | | |
|---|---|---|---|
| 9,364,297 | B2 | 6/2016 | Kitching et al. |
| 10,052,174 | B2 | 8/2018 | Kitching et al. |
| 2001/0002310 | A1 | 5/2001 | Chishti et al. |
| 2002/0006597 | A1 | 1/2002 | Andreiko et al. |
| 2002/0010568 | A1 | 1/2002 | Rubbert et al. |
| 2002/0064746 | A1 | 5/2002 | Muhammad et al. |
| 2002/0072027 | A1 | 6/2002 | Chishti |
| 2003/0009252 | A1 | 1/2003 | Pavlovskaia et al. |
| 2003/0049584 | A1 | 3/2003 | Chishti et al. |
| 2003/0139834 | A1 | 7/2003 | Nikolskiy et al. |
| 2003/0143509 | A1 | 7/2003 | Kopelman et al. |
| 2003/0190575 | A1* | 10/2003 | Hilliard ............................ 433/6 |
| 2003/0224311 | A1 | 12/2003 | Cronauer |
| 2004/0072120 | A1* | 4/2004 | Lauren .................. A61C 7/20 433/24 |
| 2004/0128010 | A1 | 7/2004 | Pavlovskaia et al. |
| 2004/0197727 | A1* | 10/2004 | Sachdeva ............... A61C 7/00 433/24 |
| 2004/0202983 | A1 | 10/2004 | Tricca et al. |
| 2005/0038669 | A1 | 2/2005 | Sachdeva et al. |
| 2005/0048432 | A1 | 3/2005 | Choi et al. |
| 2005/0055118 | A1 | 3/2005 | Nikolskiy et al. |
| 2005/0089822 | A1 | 4/2005 | Geng et al. |
| 2005/0192835 | A1 | 9/2005 | Kuo et al. |
| 2005/0241646 | A1 | 11/2005 | Sotos et al. |
| 2005/0271996 | A1 | 12/2005 | Sporbert et al. |
| 2006/0004609 | A1 | 1/2006 | Kenneth et al. |
| 2006/0079981 | A1 | 4/2006 | Rubbert et al. |
| 2006/0121408 | A1 | 6/2006 | Hedge et al. |
| 2006/0127836 | A1 | 6/2006 | Wen |
| 2006/0147872 | A1 | 7/2006 | Andreiko |
| 2006/0194163 | A1 | 8/2006 | Tricca et al. |
| 2006/0199142 | A1 | 9/2006 | Liu et al. |
| 2006/0263739 | A1 | 11/2006 | Sporbert et al. |
| 2006/0286501 | A1 | 12/2006 | Chishti et al. |
| 2007/0003900 | A1 | 1/2007 | Miller |
| 2007/0072144 | A1 | 3/2007 | Imgrund et al. |
| 2007/0099147 | A1 | 5/2007 | Sachdeva et al. |
| 2007/0184398 | A1* | 8/2007 | Cronauer .............. A61C 7/08 433/6 |
| 2007/0226005 | A1 | 9/2007 | Smith et al. |
| 2008/0050692 | A1* | 2/2008 | Hilliard .................. A61C 7/08 433/24 |
| 2008/0305452 | A1 | 12/2008 | Sterental et al. |
| 2008/0305453 | A1 | 12/2008 | Kitching et al. |
| 2008/0306724 | A1 | 12/2008 | Kitching et al. |
| 2012/0225401 | A1 | 9/2012 | Kitching et al. |
| 2014/0023980 | A1 | 1/2014 | Kitching et al. |
| 2014/0193765 | A1 | 7/2014 | Kitching et al. |
| 2014/0335466 | A1 | 11/2014 | Kitching et al. |

FOREIGN PATENT DOCUMENTS

| | | |
|---|---|---|
| AU | 5598894 | 6/1994 |
| CA | 1121955 | 4/1982 |
| DE | 2749802 | 5/1978 |
| EP | 0091876 | 10/1983 |
| EP | 0299490 | 1/1989 |
| EP | 0376873 | 7/1990 |
| EP | 0490848 | 6/1992 |
| EP | 0541500 | 5/1993 |
| EP | 0667753 | 8/1995 |
| EP | 0731673 | 9/1996 |
| EP | 0774933 | 5/1997 |
| EP | 69327661 | 7/2000 |
| ES | 463897 | 1/1980 |
| FR | 2369828 | 6/1978 |
| FR | 2652256 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 | 8/1990 |
| WO | WO 91/04713 | 4/1991 |
| WO | WO 94/10935 | 5/1994 |
| WO | WO 98/32394 | 7/1998 |
| WO | WO 98/44865 | 10/1998 |
| WO | WO 98/58596 | 12/1998 |
| WO | WO-2006065955 A2 | 6/2006 |
| WO | WO-2006118771 A2 | 11/2006 |

OTHER PUBLICATIONS

"Important Tip About Wearing the Red White & Blue Active Clear Retainer System," Allesee Orthodontic Appliances—Pro Lab, 1 page.

"Inside the ADA," JADA, 118:286-294 (Mar. 1989).

"The Choice is Clear: Red, White & Blue . . . The Simple, Affordable, No-Braces Treatment," Allesee Orthodontic Appliances—Pro Lab product information for doctors, <http://ormco.com/aoa/appliancesservices/RWB/doctor.html>, 5 pages (May 19, 2003).

"The Choice is Clear: Red, White & Blue . . . The Simple, Affordable, No-Braces Treatment," Allesee Orthodontic Appliances—Pro Lab product information for patients, <http://ormco.com/aoa/appliancesservices/RWB/patients.html>, 2 pages (May 19, 2003).

"The Choice is Clear: Red, White & Blue . . . The Simple, Affordable, No-Braces Treatment," Allesee Orthodontic Appliances—Pro Lab product information, 6 pages (2003).

"The Red, White & Blue Way to Improve Your Smile!" Allesee Orthodontic Appliances—Pro Lab product information for patients, 2 pages.

"You May Be a Candidate for This Invisible No-Braces Treatment," Allesee Orthodontic Appliances—Pro Lab product information for patients, 2 pages.

Alexander et al., "The DigiGraph Work Station Part 2 Clinical Management," JCO, pp. 402-407 (Jul. 1990).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961(1981).

Altschuler, "3D Mapping of Maxillo-Facial Prosthesis," AADR Abstract #607, 2 pages total, (1980).

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24.

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

(56) References Cited

OTHER PUBLICATIONS

Bernard et al., "Computerized Diagnosis in Orthodontics for Epidemiological Studies: A Progress Report," Abstract, *J. Dental Res. Special Issue*, vol. 67, p. 169, paper presented at International Association for Dental Research 66th General Session, Mar. 9-13, 1988, Montreal, Canada.
Bhatia et al., "A Computer-Aided Design for Orthognathic Surgery," *Br. J. Oral Maxillofac. Surg.*, 22:237-253 (1984).
Biggerstaff et al., "Computerized Analysis of Occlusion in the Postcanine Dentition," *Am. J. Orthod.*, 61(3): 245-254 (Mar. 1972).
Biggerstaff, "Computerized Diagnostic Setups and Simulations," *Angle Orthod.*, 40(1):28-36 (Jan. 1970).
Biostar Opeation & Training Manual. Great Lakes Orthodontics, Ltd. 199 Fire Tower Drive, Tonawanda, New York. 14150-5890. 20 pages total.
Blu, et al., "Linear interpolation revitalized", *IEEE Trans. Image Proc.*, 13(5):710-719 (May 2004).
Bourke, "Coordinate System Transformation," (Jun. 1996), p. 1, retrieved from the Internet Nov. 5, 2004, URL <http://astronomy.swin.edu.au/~pbourke/projection/coords>.
Boyd et al., "Three Dimensional Diagnosis and Orthodontic Treatment of Complex Malocclusions With the Invisalign Appliance," *Semin. Orthod.*, 7(4):274-293 (Dec. 2001).
Brandestini et al., "Computer Machined Ceramic Inlays: In Vitro Marginal Adaptation," *J. Dent. Res. Special Issue*, Abstracts, vol. 64, p. 208 (1985).
Brook et al., "An Image Analysis System for the Determination of Tooth Dimensions from Study Casts: Comparison with Manual Measurements of Mesio-distal Diameter," *J. Dent. Res.*, 65(3):428-431 (Mar. 1986).
Burstone (interview), "Dr. Charles J. Burstone on the Uses of the Computer in Orthodontic Practice (Part 1)," *J. Clin. Orthod.*, 13(7):442-453 (Jul. 1979).
Burstone (interview), "Dr. Charles J. Burstone on the Uses of the Computer in Orthodontic Practice (Part 2)," *J. Clin. Orthod.*, 13(8):539-551 (Aug. 1979).
Burstone et al., Precision Adjustment of the Transpalatal Lingual Arch: Computer Arch Form Predetermination, *Am, Journal of Orthodontics*, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," *JCO*, pp. 360-367 (Jun. 1990).
Chafetz et al., "Subsidence of the Femoral Prosthesis, A Stereophotogrammetric Evaluation," *Clin. Orthop. Relat. Res.*, No. 201, pp. 60-67 (Dec. 1985).
Chiappone, (1980). Constructing the Gnathologic Setup and Positioner, *J. Clin. Orthod*, vol. 14, pp. 121-133.
Cottingham, (1969). Gnathologic Clear Plastic Positioner, *Am. J. Orthod*, vol. 55, pp. 23-31.
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, *Canadian Dental Journal*, vol. 54(9), pp. 661-666 (1988).
Crawford, "CAD/CAM in the Dental Office: Does it Work?", *Canadian Dental Journal*, vol. 57, No. 2, pp. 121-123 (Feb. 1991).
Crooks, "CAD/CAM Comes to USC," *USC Dentistry*, pp. 14-17 (Spring 1990).
Cureton, Correcting Malaligned Mandibular Incisors with Removable Retainers, *J. Clin. Orthod*, vol. 30, No. 7 (1996) pp. 390-395.
Curry et al., "Integrated Three-Dimensional Craniofacial Mapping at the Craniofacial Research Instrumentation Laboratory/University of the Pacific," *Semin. Orthod.*, 7(4):258-265 (Dec. 2001).
Cutting et al., "Three-Dimensional Computer-Assisted Design of Craniofacial Surgical Procedures: Optimization and Interaction with Cephalometric and CT-Based Models," *Plast. Reconstr. Surg.*, 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for "Gingiva," Dictionary.com, pp. 1-3, retrieved from the Internet on Nov. 5, 2004, URL <http://reference.com/search/search?g=gingiva>.
DeFranco et al., "Three-Dimensional Large Displacement Analysis of Orthodontic Appliances," *J. Biomechanics*, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13.
DENT-X posted on Sep. 24, 1998 at <http://www.dent-x.com/DentSim.htm>, 6 pages.
Doyle, "Digital Dentistry," *Computer Graphics World*, pp. 50-52, 54 (Oct. 2000).
DuraClear™ product information, Allesee Orthodontic Appliances—Pro Lab, 1 page.
Duret et al, "CAD-CAM in Dentistry," *J. Am. Dent. Assoc.*, 117:715-720 (Nov. 1988).
Duret et al., "CAD/CAM Imaging in Dentistry," *Curr. Opin. Dent.*, 1:150-154 (1991).
Duret, "The Dental CAD/CAM, General Description of the Project," *Hennson International Product Brochure*, 18 pages total, Jan. 1986.
Duret,"Vers Une Prosthese Informatisee," (English translation attached), *Tonus*, vol. 75, pp. 55-57 (Nov. 15, 1985).
Economides, "The Microcomputer in the Orthodontic Office," *JCO*, pp. 767-772 (Nov. 1979).
Elsasser, Some Observations on the History and Uses of the Kesling Positioner, *Am. J. Orthod.* (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," *Am. J. Orthod.*, 73(1):36-46 (Jan. 1978).
Felton et al., "A Computerized Analysis of the Shape and Stability of Mandibular Arch Form," *Am. J. Orthod. Dentofacial Orthop.*, 92(6):478-483 (Dec. 1987).
Friede et al., "Accuracy of Cephalometric Prediction in Orthognathic Surgery," Abstract of Papers, *J. Dent. Res.*, 70:754-760 (1987).
Fütterling et al., "Automated Finite Element Modeling of a Human Mandible with Dental Implants," WSCG '98—Conference Program, retrieved from the Internet: <http://wscg.zcu.cz/wscg98/papers98/Strasser_98.pdf>, 8 pages.
Gao et al., "3-D element Generation for Multi-Connected Complex Dental and Mandibular Structure," Proc. Int'l. Workshop on Medical Imaging and Augmented Reality, pp. 267-271 (Jun. 12, 2001).
Gim-Alldent Deutschland, "Das DUX System: Die Technik," 2 pages total.
Gottleib et al., "JCO Interviews Dr. James A. McNamura, Jr., on the Frankel Appliance: Part 2: Clinical Management,"*J. Clin. Orthod.*, 16(6):390-407 (Jun. 1982).
Grayson, "New Methods for Three Dimensional Analysis of Craniofacial Deformity, Symposium: Computerized Facial Imaging in Oral and Maxiiofacial Surgery," *AAOMS*, 3 pages total, (Sep. 13, 1990).
Guess et al., "Computer Treatment Estimates in Orthodontics and Orthognathic Surgery," *JCO*, pp. 262-28 (Apr. 1989).
Heaven et al., "Computer-Based Image Analysis of Artificial Root Surface Caries," Abstracts of Papers, *J. Dent. Res.*, 70:528 (Apr. 17-21, 1991).
Highbeam Research, "Simulating Stress Put on Jaw," Tooling & Production [online], Nov. 1996, pp. 1-2, retrieved from the Internet on Nov. 5, 2004, URL <http://static.highbeam.com/t/toolingamp-production/november011996/simulatingstressputonja...>.
Hikage, "Integrated Orthodontic Management System for Virtual Three-Dimensional Computer Graphic Simulation and Optical Video Image Database for Diagnosis and Treatment Planning", *Journal of Japan Orthodontic Society*, Feb. 1987, English translation, pp. 1-38, Japanese version, 46(2), pp. 248-269 (60 pages total).

(56) References Cited

OTHER PUBLICATIONS

Hoffmann, et al., "Role of Cephalometry for Planning of Jaw Orthopedics and Jaw Surgery Procedures," (Article Summary in English, article in German), *Informatbnen*, pp. 375-396 (Mar. 1991).

Hojjatie et al., "Three-Dimensional Finite Element Analysis of Glass-Ceramic Dental Crowns," *J. Biomech.*, 23(11):1157-1166 (1990).

Huckins, "CAD-CAM Generated Mandibular Model Prototype from MRI Data," *AAOMS*, p. 96 (1999).

"JCQ Interviews, Craig Andreiko, DDS, MS on the Elan and Orthos Systems," *JCO*, pp. 459-468 (Aug. 1994).

"JCO Interviews, Dr. Homer W. Phillips on Computers in Orthodontic Practice, Part 2," *JCO*, pp. 819-831 (Dec. 1983).

Jerrold, "The Problem, Electronic Data Transmission and the Law," *AJO-DO*, pp. 478-479 (Apr. 1988).

Jones et al., "An Assessment of the Fit of a Parabolic Curve to Pre- and Post-Treatment Dental Arches," *Br. J. Orthod.*, 16:85-93 (1989).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case Reports, J. Nihon University School of Dentistry (1982) 24(1):1-27.

Kanazawa et al., "Three-Dimensional Measurements of the Occlusal Surfaces of Upper Molars in a Dutch Population," *J. Dent Res.*, 63(11):1298-1301 (Nov. 1984).

Kochanek, "Interpolating Splines with Local Tension, Continuity and Bias Control," *Computer Graphics*, 18(3):33-41 (Jul. 1984).

Kesling et al., The Philosophy of the Tooth Positioning Appliance, *American Journal of Orthodontics and Oral Surgery* (1945) 31:297-304.

Kesling, Coordinating the Predetermined Pattern and Tooth Positioner with Conventional Treatment, *Am. J. Orthod. Oral Surg.* (1946) 32:285-293.

Kleeman et al., The Speed Positioner, *J. Clin. Orthod.* (1996) 30:673-680.

Kunii et al., "Articulation Simulation for an Intelligent Dental Care System," *Displays* 15:181-188 (1994).

Kuroda et al., Three-Dimensional Dental Cast Analyzing System Using Laser Scanning, *Am. J. Orthod. Dentofac. Orthop.* (1996) 110:365-369.

Laurendeau, et al., "A Computer-Vision Technique for the Acquisition and Processing of 3-D Profiles of Dental Imprints: An Application in Orthodontics," *IEEE Transactions on Medical Imaging*, 10(3):453-461 (Sep. 1991).

Leinfelder, et al., "A New Method for Generating Ceramic Restorations: a CAD-CAM System," *J. Am. Dent. Assoc.*, 118(6):703-707 (Jun. 1989).

Manetti, et al., "Computer-Aided Cefalometry and New Mechanics in Orthodontics," (Article Summary in English, article in German), *Fortschr. Kieferorthop.* 44, 370-376 (Nr. 5), 1983.

McCann, "Inside the ADA," *J. Amer. Dent. Assoc.*, 118:286-294 (Mar. 1989).

McNamara et al., "Invisible Retainers," *J. Clin. Orthod.*, pp. 570-578 (Aug. 1985).

McNamara et al., *Orthodontic and Orthopedic Treatment in the Mixed Dentition*, Needham Press, pp. 347-353 (Jan. 1993).

Moermann et al., "Computer Machined Adhesive Porcelain Inlays: Margin Adaptation after Fatigue Stress," IADR Abstract 339, *J. Dent. Res.*, 66(a):763 (1987).

Moles, "Correcting Mild Malalignments—As Easy as One, Two, Three," *AOA/Pro Corner*, 2 pages.

Mörmann et al., "Marginale Adaptation von adhäsuven Porzellaninlays in vitro," Separatdruck aus: Schweiz. Mschr. Zahnmed. 95: 1118-1129, 1985.

Nahoum, "The Vacuum Formed Dental Contour Appliance," *N. Y. State Dent. J.*, 30(9):385-390 (Nov. 1964).

Nash, "CEREC CAD/CAM Inlays: Aesthetics and Durability in a Single Appointment," *Dent. Today*, 9(8):20, 22-23 (Oct. 1990).

Nishiyama et al., "A New Construction of Tooth Repositioner by LTV Vinyl Silicone Rubber," *J. Nihon Univ. Sch. Dent.*, 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," *Dentist*, 3 pages total, Jan./Feb. 1989.

Pinkham, "Inventor's CAD/CAM May Transform Dentistry," *Dentist*, 3 pages total, Sep. 1990.

Ponitz, "Invisible Retainers," *Am. J. Orthod.*, 59(3):266-272 (Mar. 1971).

Procera Research Projects, "Procera Research Projects 1993—Abstract Collection," pp. 3-28 (1993).

Proffit et al., *Contemporary Orthodontics*, (Second Ed.), Chapter 15, Mosby Inc., pp. 470-533 (Oct. 1993).

Raintree Essix & ARS Materials, Inc., Raintree Essix, Technical Magazine Table of contents and Essix Appliances, <httpz;// www.essix.com/magazine/default.html> Aug. 13, 1997, 7 pages.

Redmond et al., "Clinical Implications of Digital Orthodontics," *Am. J. Orthod. Dentofacial Orthop.*, 117(2):240-242 (2000).

Rekow et al., "CAD/CAM for Dental Restorations—Some of the Curious Challenges," *IEEE Trans. Biomed. Eng.*, 38(4):344-345 (Apr. 1991).

Rekow et al., "Comparison of Three Data Acquisition Techniques for 3-D Tooth Surface Mapping," *Annual International Conference of the IEEE Engineering in Medicine and Biology Society*, 13(1):344-345.

Rekow, "A Review of the Developments in Dental CAD/CAM Systems," (contains references to Japanese efforts and content of the papers of particular interest to the clinician are indicated with a one-line summary of their content in the bibliography), *Curr. Opin. Dent.*, 2:25-33 (Jun. 1992).

Rekow, "CAD/CAM in Dentistry: A Historical Perspective and View of the Future," *J. Can. Dent. Assoc.*, 58(4):283, 287-288 (Apr. 1992).

Rekow, "Computer-Aided Design and Manufacturing in Dentistry: A Review of the State of the Art," *J. Prosthet. Dent.*, 58(4):512-516 (Oct. 1987).

Rekow, "Dental CAD-CAM Systems: What is the State of the Art?", *J. Amer. Dent. Assoc.*, 122:43-48 (1991).

Rekow, "Feasibility of an Automated System for Production of Dental Restorations, Ph.D. Thesis," Univ. of Minnesota, 244 pages total, Nov. 1988.

Richmond et al., "The Development of the PAR Index (Peer Assessment Rating): Reliability and Validity," *Eur. J. Orthod.*, 14:125-139 (1992).

Richmond et al., "The Development of a 3D Cast Analysis System," *Br. J. Orthod.*, 13(1):53-54 (Jan. 1986).

Richmond, "Recording the Dental Cast in Three Dimensions," *Am. J. Orthod. Dentofacial Orthop.*, 92(3):199-206 (Sep. 1987).

Rudge, "Dental Arch Analysis: Arch Form, A Review of the Literature," *Eur. J. Orthod.*, 3(4):279-284.

Sakuda et al., "Integrated Information-Processing System in Clinical Orthodontics: An Approach with Use of a Computer Network System," *Am. J. Orthod. Dentofacial Orthop.*, 101(3): 210-220 (Mar. 1992).

Schellhas et al., "Three-Dimensional Computed Tomography in Maxillofacial Surgical Planning," *Arch. Otolamgol. Head Neck Surg.*, 114:438-442 (Apr. 1988).

Schroeder et al., Eds. *The Visual Toolkit*, Prentice Hall PTR, New Jersey (1998) Chapters 6, 8 & 9, (pp. 153-210,309-354, and 355-428, respectively).

Shilliday, (1971). Minimizing finishing problems with the mini-positioner, *Am. J. Orthod.* 59:596-599.

Siemens, "CEREC—Computer-Reconstruction," High Tech in der Zahnmedizin, 14 pages total.

Sinclair, "The Readers' Corner," *J. Clin. Orthod.*, 26(6):369-372 (Jun. 1992).

Sirona Dental Systems GmbH, *CEREC 3D, Manuel utiiisateur*, Version 2.0X (in French), 2003,114 pages total.

(56) References Cited

OTHER PUBLICATIONS

Stoll et al., "Computer-aided Technologies in Dentistry," (article summary in English, article in German), *Dtsch Zahna'rztl Z* 45, pp. 314-322 (1990).
Sturman, "Interactive Keyframe Animation of 3-D Articulated Models," Proceedings Graphics Interface '84, May-Jun. 1984, pp. 35-40.
Truax L., "Truax Clasp-Less(TM) Appliance System," *Funct. Orthod.*, 9(5):22-4, 26-8 (Sep.-Oct. 1992).
Tru-Tain Orthodontic & Dental Supplies, Product Brochure, Rochester, Minnesota 55902, 16 pages total.
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050342, filed Jun. 20, 1997, 41 pages total.
Van Der Linden et al., "Three-Dimensional Analysis of Dental Casts by Means of the Optocom," *J. Dent. Res.*, p. 1100 (Jul.-Aug. 1972).
Van Der Linden, "A New Method to Determine Tooth Positions and Dental Arch Dimensions," *J. Dent. Res.*, 51(4):1104 (Jul.-Aug. 1972).
Van Der Zel, "Ceramic-Fused-to-Metal Restorations with a New CAD/CAM System," *Quintessence Int.*, 24(11):769-778 (1993).
Varady et al., "Reverse Engineering of Geometric Models—An Introduction," *Computer-Aided Design*, 29(4):255-268,1997.
Verstreken et al., "An Image-Guided Planning System for Endosseous Oral Implants," *IEEE Trans. Med. Imaging*, 17(5):842-852 (Oct. 1998).
Warunek et al., Physical and Mechanical Properties of Elastomers in Orthodonic Positioners, *Am J. Orthod. Dentofac. Orthop*, vol. 95, No. 5, (May 1989) pp. 399-400.
Warunek et.al., Clinical Use of Silicone Elastomer Applicances, *JCO* (1989) XXIII(10):694-700.
Wells, Application of the Positioner Appliance in Orthodontic Treatment, *Am. J. Orthodont.* (1970) 58:351-366.
Williams, "Dentistry and CAD/CAM: Another French Revolution," *J. Dent. Practice Admin.*, pp. 2-5 (Jan./Mar. 1987).
Williams, "The Switzerland and Minnesota Developments in CAD/CAM," *J. Dent. Practice Admin.*, pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL <http://wscg.zcu.cz/wscg98/wscg98.h>.
Xia et al., "Three-Dimensional Virtual-Reality Surgical Planning and Soft-Tissue Prediction for Orthognathic Surgery," *IEEE Trans. Inf. Technol. Biomed.*, 5(2):97-107 (Jun. 2001).
Yamamoto et al., "Optical Measurement of Dental Cast Profile and Application to Analysis of Three-Dimensional Tooth Movement in Orthodontics," *Front. Med. Biol. Eng.*, 1(2):119-130 (1988).
Yamamoto et al., "Three-Dimensional Measurement of Dental Cast Profiles and its Applications to Orthodontics," *Conf. Proc. IEEE Eng. Med. Biol. Soc.*, 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," *Nippon Dental Review*, 452:61-74 (Jun. 1980).
Yoshii, "Research on a New Orthodontic Appliance: The Dynamic Positioner (D.P.); II. The D.P. Manufacturing Procedure and Clinical Applications," *Nippon Dental Review*, 454:107-130 (Aug. 1980).
Yoshii, "Research on a New Orthodontic Appliance: The Dynamic Positioner (D.P.); III.—The General Concept of the D.P. Method and its Therapeutic Effect, Part 2. Skeletal Reversed Occlusion Case Reports," *Nippon Dental Review*, 458:112-129 (Dec. 1980).
Yoshii, "Research on a New Orthodontic Appliance: The Dynamic Positioner (D.P.); III. The General Concept of the DP. Method and its Therapeutic Effect, Part 1, Dental and Functional Reversed Occlusion Case Reports," *Nippon Dental Review*, 457:146-164 (Nov. 1980).
Richmond, et al. A 2-Center Comparison of Orthodontist's Perceptions of Orthodontic Treatment Difficulty. Jan. 2001, Angle Orthodontist, vol. 71, No. 5, pp. 404-410.
European search report with written opinion dated Mar. 7, 2017 for EP16197945.5.

\* cited by examiner

Cosmetic Treatment Service — 352
Patient: Name   LastName

Begin   Review Case Setup   View Appointments   Progress Track 1   Progress Track 2   End
        View Virtual TxPlan Review Case Setup: — 354

This case has qualified for treatment through the Cosmetic Treatment Service.

Lab Fees:                          $_____.00
Estimated Duration:                15 – 20 aligners (30 – 40 weeks)
Appointment Planning Schedule:     Click here to view in ClinCheck® software
                                   _____

*If you wish to change treatment goals or other specific aspects of this treatment please switch to the Invisalign Custom Treatment Options. Click "cancel" to cancel this case.* — 356

☐ I understand...         [ I Accept This Treatment ] — 358

[ Cancel Case ]

FIG. 5

TREATMENT PLANNING AND PROGRESS TRACKING SYSTEMS AND METHODS

CROSS-REFERENCES TO RELATED APPLICATIONS

This application is a continuation-in-part of U.S. application Ser. No. 11/760,701, entitled "Treatment Planning and Progress Tracking Systems and Methods," filed on Jun. 8, 2007, which is related to U.S. application Ser. No. 11/760,689, entitled "Systems And Method for Management And Delivery Of Orthodontic Treatment," filed on Jun. 8, 2007, now U.S. Pat. No. 9,060,829, issued on Jun. 23, 2015; U.S. application Ser. No. 11/760,705, entitled "Treatment Progress Tracking And Recalibration," filed on Jun. 8, 2007, now U.S. Pat. No. 8,562,338, issued on Oct. 22, 2013; and U.S. application Ser. No. 11/760,612, entitled "System And Method For Detecting Deviations During The Course Of An Orthodontic Treatment To Gradually Reposition Teeth," filed on Jun. 8, 2007, now U.S. Pat. No. 8,075,306, issued on Dec. 13, 2011; the full disclosures of which are incorporated herein by reference.

BACKGROUND OF THE INVENTION

The present invention relates generally to the field of orthodontics, and more particularly to systems and methods of managing planning and delivery of an orthodontic treatment using planning tools, treatment guidelines, instructions and appointment planning tools customized to the individual patient being treated, as well as tools and methods for tracking delivery and patient progression through an orthodontic treatment plan.

An objective of orthodontics is to move a patient's teeth to positions where function and/or aesthetics are optimized. Traditionally, appliances such as braces are applied to the patient's teeth by an orthodontist or dentist and the set of braces exerts continual force on the teeth and gradually urges them toward their intended positions. Over time and with a series of clinical visits and adjustments to the braces, the practitioner adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, Calif., under the tradename Invisalign® System. The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as ClinCheck® from Align Technology, Inc. The design of the aligners can rely on computer modeling of a series of planned successive tooth arrangements, and the individual aligners are designed to be worn over the teeth and elastically reposition the teeth to each of the planned tooth arrangements.

Recent advances in orthodontic treatment, including availability of the treatment systems discussed above, have made orthodontic treatment options available to a wide variety of patients and dental practitioners. Unfortunately, barriers to more wide-spread use of such treatment options still exist, thereby preventing both patients and dental practitioners from access to orthodontic treatment technology they desire. One such barrier includes more wide-spread use of orthodontic treatment technology to dental practitioners with limited experience in orthodontics. For example, many general dental practitioners with limited knowledge or exposure to orthodontics may be interested in learning orthodontic techniques and providing such treatment to patients, but may lack confidence in their abilities to effectively deliver treatment and/or achieve predictable outcomes. Furthermore, while patient treatment and tooth movements can be planned prospectively, in some cases orthodontic treatment can deviate from the planned treatment or stages, which can be challenging to practitioners of any experience level and can lead to variability in treatment outcome and, in many cases, decreased treatment efficacy. Deviations can arise for numerous reasons, and can include biological variations, poor patient compliance, and/or factors related to biomechanical design. In the case of aligners, continued treatment with previously designed and/or fabricated aligners can be difficult or impossible where a patient's teeth deviate substantially from the planned treatment course. For example, subsequent aligners may no longer fit the patient's teeth once treatment progression has deviated from the planned course.

Accordingly, improved methods and techniques are needed for facilitating orthodontic practice among a wide range of practitioners, including those with limited experience in orthodontics as well as experienced practitioners desiring more guidance particularly for complex cases. Furthermore, because detecting a deviation from planned treatment most typically relies on visual inspection of the patient's teeth or observation of appliances no longer fitting, treatment can sometimes progresses significantly off track by the time a deviation is detected, thereby making any required corrective measures more difficult and/or substantial. Treatment planning an management systems that can provide earlier and better off track determinations, together with other enhanced planning and management tools, would, therefore, be beneficial.

BRIEF SUMMARY OF THE INVENTION

The present invention provides systems and methods of managing planning and delivery of an orthodontic treatment using enhanced treatment planning options and features including appointment planning tools and guidelines, and treatment progress tracking features, where options can be specifically customized to the individual patient being treated. Systems and methods of managing orthodontic treatment as disclosed herein can be included or incorporated in a variety of orthodontic treatment regimens including, for example, treatment according to the Invisalign® System. Treatment can be planned proactively or pre-planned for administration to a patient in a series of one or more phases, with at least some of the phases including a set of appliances that are worn successively by the patient to reposition the teeth through pre-planned arrangements and eventually toward a selected final arrangement. Planned treatment phases can include customized treatment guidelines tailored to the particular treatment plan generated for the patient being treated, the guidelines being useful in helping to more effectively manage delivery and treatment of the patient according to the treatment plan. Additionally, progress tracking features can be incorporated into a pre-planned treatment for monitoring and management of treatment delivery and progress, and to provide enhanced detection and feedback as to whether treatment is progressing as planned. Treatment plan options can be provided in a treatment plan individually or in a pre-selected bundle or package of options, and may be provided based on an expressed desired by the patient or practitioner or based on screening or case assessments and resulting recommendations or suitable corresponding options.

Thus, in one aspect, the present invention includes methods and systems of managing delivery of an orthodontic treatment plan. A method can include, for example, generating a case difficulty assessment based on information received, generating a treatment plan for a patient, providing customized set(s) of treatment guidelines, and tracking progression of the patient's teeth along a treatment path or according to the treatment plan. In another example, a method can include receiving information indicating a dental condition of a patient or a treatment goal, providing the practitioner with a selection of enhanced treatment plan options including, for example, phased treatment deliver, appointment planning tools, and progress tracking features. A system can include, for example, a computer coupled to a server, the computer comprising a processor and a computer readable medium comprising instructions which, if executed, cause the computer to generate a case assessment, generate a treatment plan for a patient, generate a customized set of treatment guidelines, and generate progress tracking information, for example, a determination of whether an actual arrangement of the patient's teeth deviates from a planned tooth arrangement.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 5 shows a user interface illustrating results of an assessment and additional information, according to an embodiment of the present invention.

DETAILED DESCRIPTION OF THE INVENTION

The present invention provides improved systems and methods of managing deliver of an orthodontic treatment plan using proactive treatment planning and enhanced treatment planning tools including, for example, customized treatment guidelines and appointment planning tools, and treatment progress monitoring and tracking techniques. Systems and methods of the present invention can be included in a variety of orthodontic treatment regimens. For example, the progress tracking and revised planning features can be optionally included and incorporated into other aspects of treatment according to the Invisalign® System. Treatment can be pre-planned for administering to a patient in a series of one or more phases, with at least some phases each including a set of appliances that are worn successively by the patient to reposition the teeth through planned arrangements and eventually toward a selected final arrangement. Enhanced treatment options (e.g., case assessment, appointment planning, progress tracking, etc.), according to the present invention, can be incorporated into the pre-planned treatment to provide a more comprehensive system for treatment planning, monitoring and management.

Figure 1:
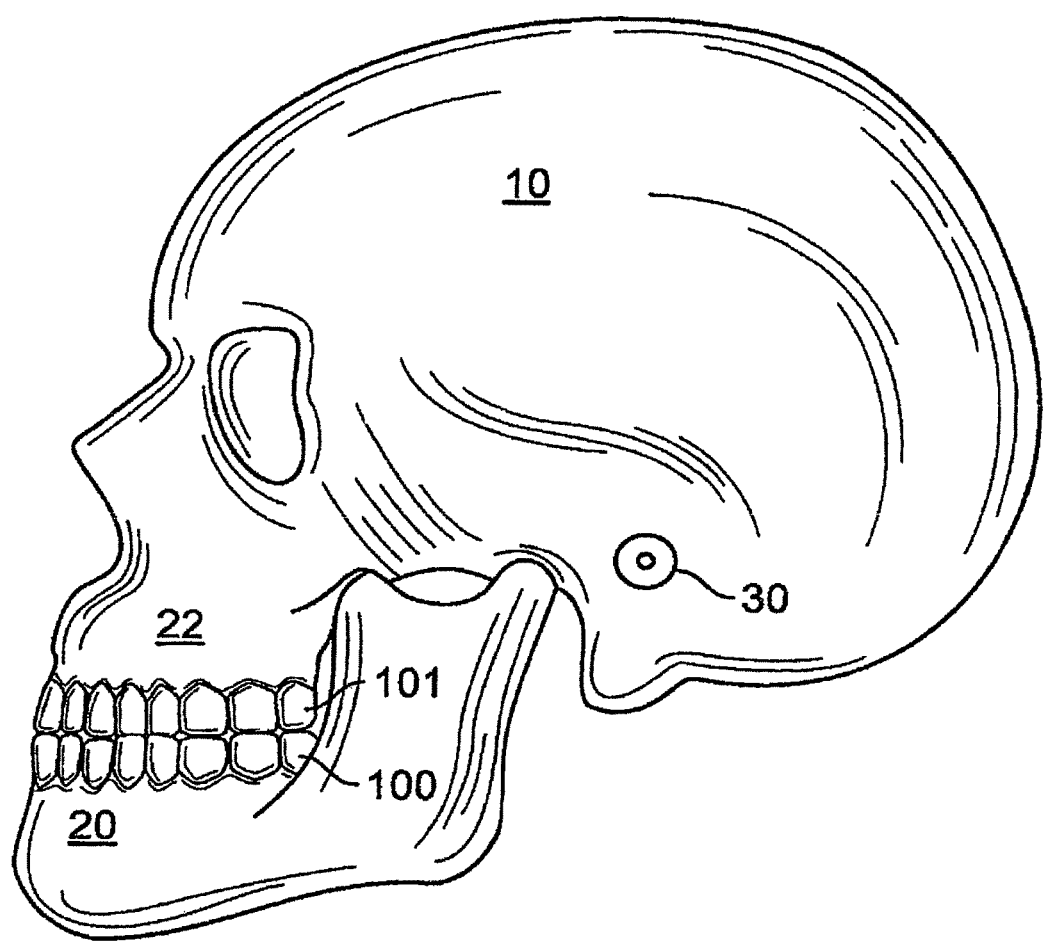
FIG. 1 is a diagram showing the anatomical relationship of the jaws of a patient.

FIG. 1 shows a skull 10 with an upperjaw bone 22 and a lowerjaw bone 20. The lowerjaw bone 20 hinges at a joint 30 to the skull 10. The joint 30 is called a temporal mandibular joint (TMJ). The upperjaw bone 22 is associated with an upper jaw 101, while the lower jaw bone 20 is associated with a lower jaw 100. A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
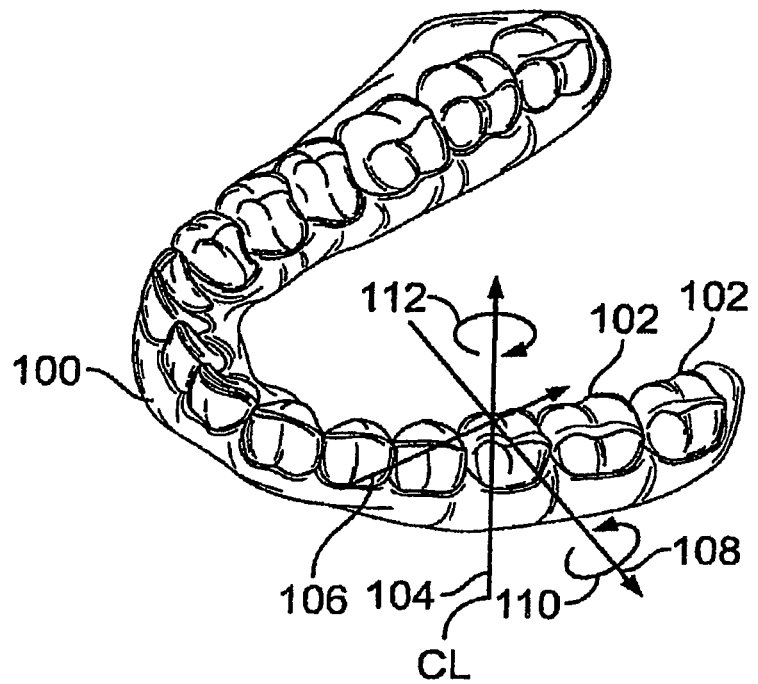
FIG. 2A illustrates in more detail the patient's lower jaw and provides a general indication of how teeth may be moved according to an embodiment of the present invention.

Referring now to FIG. 2A, the lower jaw 100 includes a plurality of teeth 102, for example, At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may-be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 112. Thus, all possible free-form motions of the tooth can be performed.

Figure 2B:
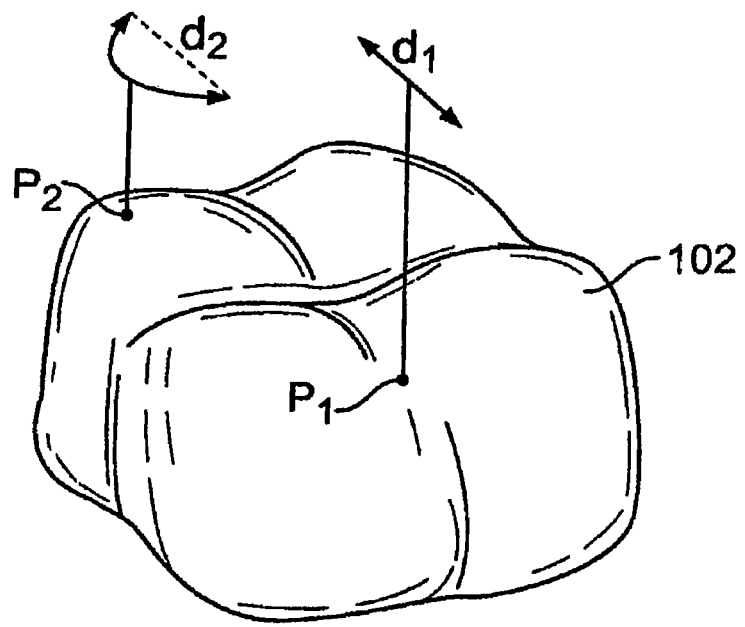
FIG. 2B illustrates a single tooth from FIG. 2A and defines determination of tooth movement distance according to an embodiment of the present invention.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitration point P2 may travel along an accurate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

Figure 2C:
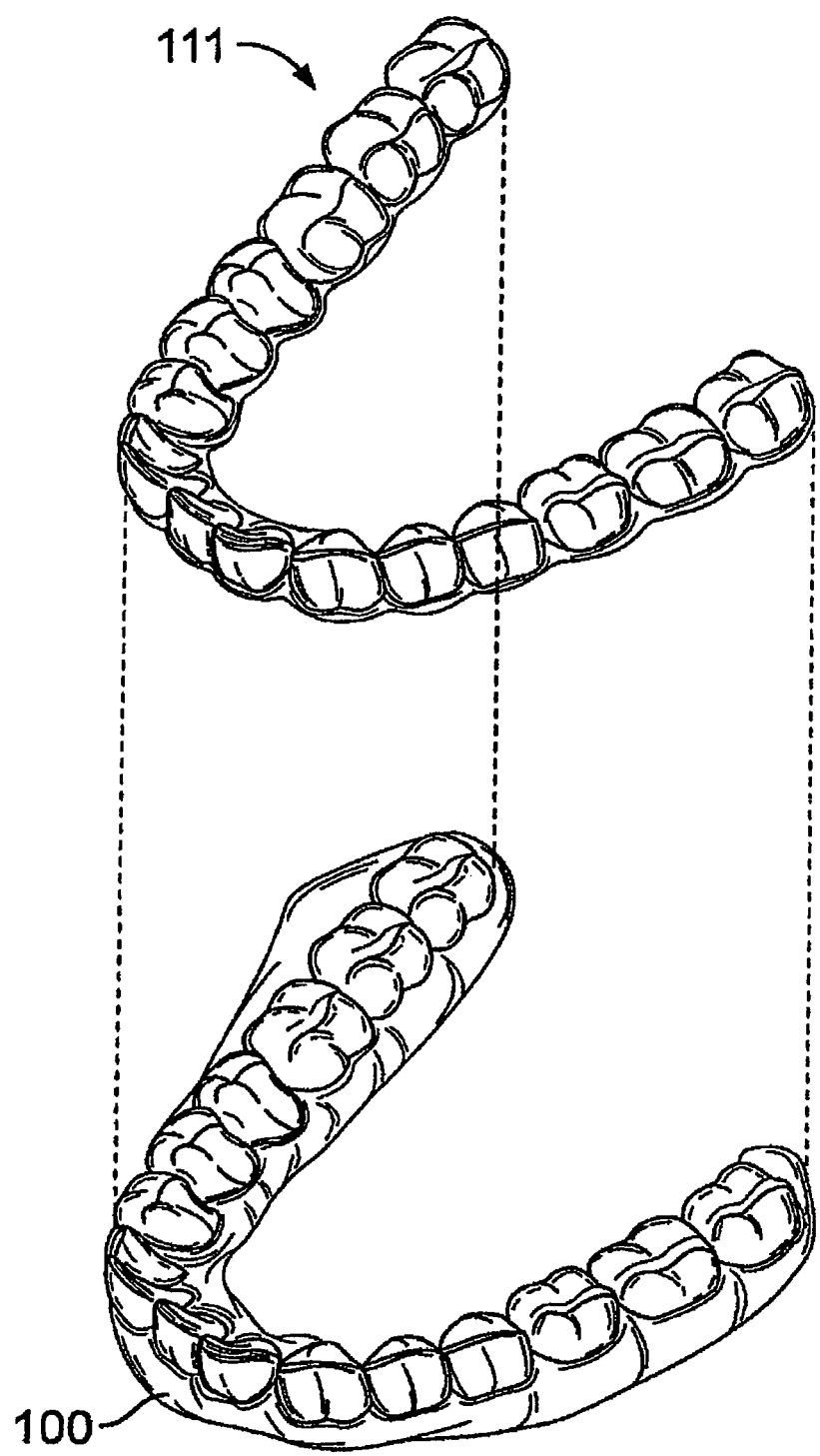
FIG. 2C illustrates the jaw of FIG. 2A together with an incremental positioning adjustment appliance according to an embodiment of the present invention.

FIG. 2C shows one adjustment appliance 111 which is worn by the patient in order to achieve an incremental repositioning of individual teeth in the jaw as described generally above. The appliance can include a shell (e.g., polymeric shell) having teeth-receiving cavities that receive and resiliently reposition the teeth. Such appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www.aligntech.com").

As set forth in the prior applications, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The appliances can be generated all at the same stage or in sets or batches, e.g., at the beginning of a stage of the treatment, and the patient wears each appliance until the pressure of each appliance on the teeth has resulted in the maximum allowable tooth movement for that given stage. A plurality of different appliances (e.g., set) can be designed and even fabricated prior to the patient wearing any appliance of the plurality. At that point, the patient replaces the current appliance with the next appliance in the series until no more appliances remain. The appliances are generally not affixed to the teeth and the patient may place and replace the appliances at any time during the procedure.

The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 3A:
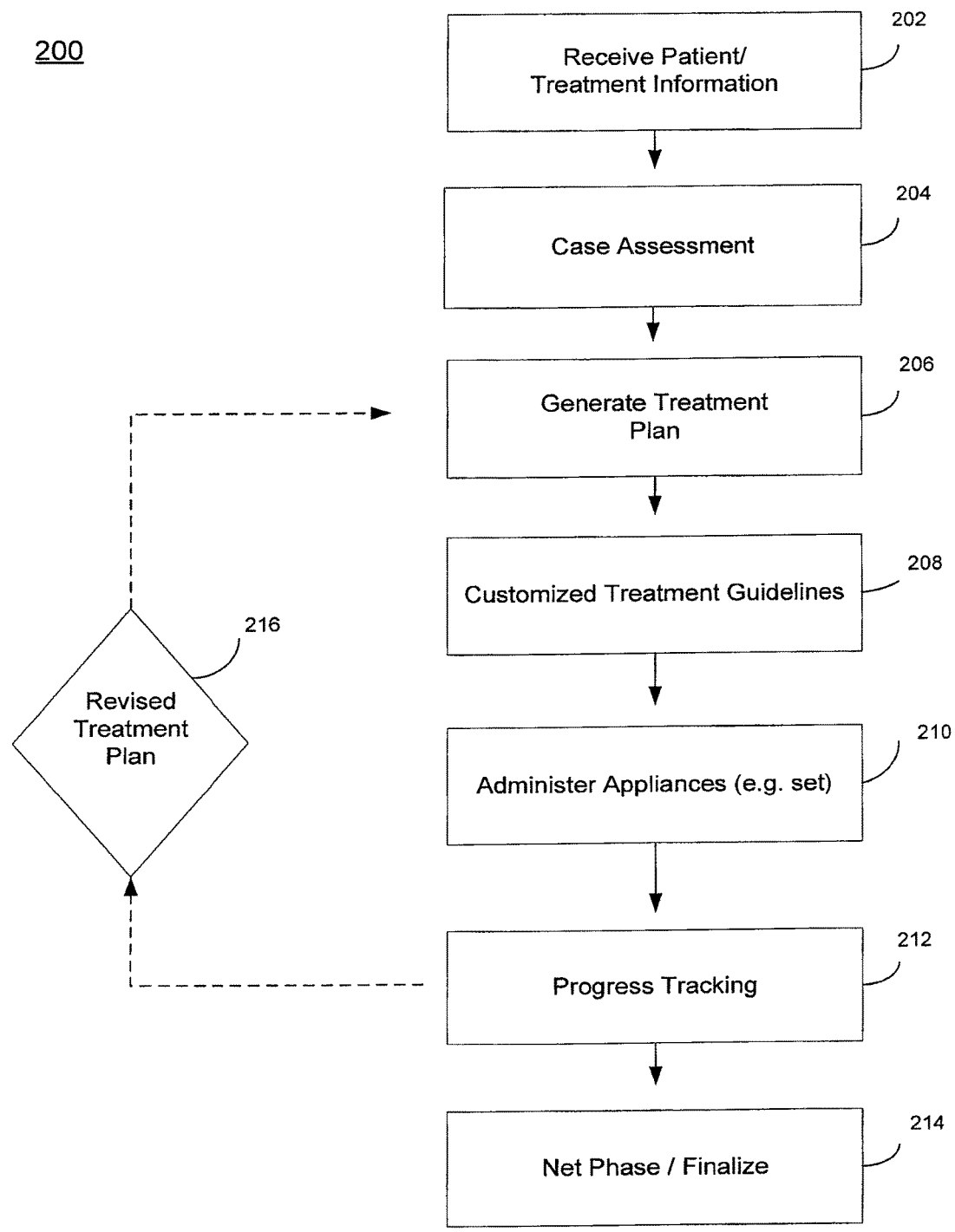
FIG. 3A shows generating and administering treatment according to an embodiment of the present invention.

Referring to FIG. 3A, a process 200 according to the present invention is illustrated. Individual aspects of the process are discussed in further detail below. The process includes receiving information regarding the orthodontic condition of the patient and/or treatment information (Step 202), generating an assessment of the case (Step 204), and generating a treatment plan for repositioning a patient's teeth (Step 206). Briefly, a patient/treatment information will include obtaining data comprising an initial arrangement of the patient's teeth, which typically includes obtaining an impression or scan of the patient's teeth prior to the onset of treatment and can further include identification of one or more treatment goals selected by the practitioner and/or patient. A case assessment can be generated (Step 204) so as to assess the complexity or difficulty of moving the particular patient's teeth in general or specifically corresponding to identified treatment goals, and may further include practitioner experience and/or comfort level in administering the desired orthodontic treatment. In some cases, however, the assessment can include simply identifying particular treatment options (e.g., appointment planning, progress tracking, etc.) that are of interest to the patient and/or practitioner. The information and/or corresponding treatment plan will include identifying a final or target arrangement of the patient's teeth that is desired, as well as a plurality of planned successive or intermediary tooth arrangements for moving the teeth along a treatment path from the initial arrangement toward the selected final or target arrangement.

The process further includes generating customized treatment guidelines (Step 208). The treatment plan typically includes multiple phases of treatment, with a customized set of treatment guidelines generated that correspond to a phase of the treatment plan. The guidelines will include detailed information on timing and/or content (e.g., specific tasks) to be completed during a given phase of treatment, and will be of sufficient detail to guide a practitioner, including a less experienced practitioner or practitioner relatively new to the particular orthodontic treatment process, through the phase of treatment. Since the guidelines are designed to specifically correspond to the treatment plan and provide guidelines on activities specifically identified in the treatment information and/or generated treatment plan, the guidelines are said to be customized. The customized treatment guidelines are then provided to the practitioner so as to help instruct the practitioner as how to deliver a given phase of treatment. As set forth above, appliances can be generated based on the planned arrangements and will be provided to the practitioner and ultimately administered to the patient (Step 210). The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of treatment guidelines, or appliances and guidelines can be provided separately.

After the treatment according to the plan begins and following administration of appliances to the patient, treatment progress tracking, e.g., by teeth matching, is done to assess a current and actual arrangement of the patient's teeth compared to a planned arrangement (Step 212). If the patient's teeth are determined to be "on-track" and progressing according to the treatment plan, then treatment progresses as planned and treatment progresses to a next stage of treatment (Step 214). If the patient's teeth have substantially reached the initially planned final arrangement, then treatment progresses to the final stages of treatment (Step 214). Where the patient's teeth are determined to be tracking according to the treatment plan, but have not yet reached the final arrangement, the next set of appliances can be administered to the patient. If, on the other hand, the patient's teeth are determined at the progress tracking step (Step 212) not to be tracking with the treatment plan, then treatment is characterized as "off-track" and an assessment is made as to how further treatment of the patient will proceed. Typically, a revised treatment plan will be generated (Step 216), and may be selected, for example, to reposition the teeth from the current position to a final position, which may be the same destination as the initially determined final position according to the initial treatment plan.

Figure 3B:
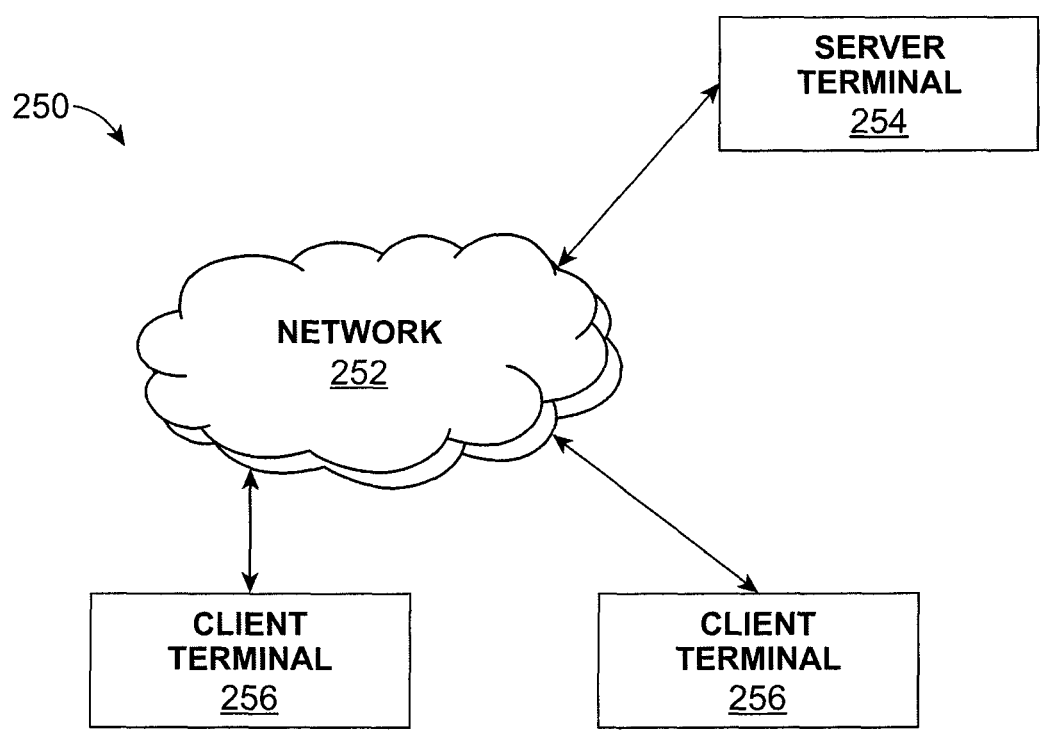
FIG. 3B is a block diagram illustrating a system according to an embodiment of the present invention.

FIG. 3B is a block diagram illustrating a network based treatment planning and management system according to one embodiment of the present invention. Referring to FIG. 3B, the system 250 includes a data network 252 and a server terminal 254 operatively coupled to the network 252. One or more client terminals 256 can be included and operatively coupled to the network 252. Client terminals 256 can include, for example, a computer terminal (e.g., personal computer) and the server terminal 254 can be configured to communicate with the one or more client terminals 256 over the network 252 to both transmit and receive information related to patient treatment as described herein, including initial patient treatment information, assessment data, appointment planning data, progress tracking data, etc. The server terminal 254 will be accessible by a third party participant in the process of the invention, in addition to the practitioner, that can at least partially participate in one or more of steps of the process (e.g., assessment, treatment plan and/or guideline generation, progress tracking, appliance design and/or manufacture, etc.). Systems can optionally include non-network based systems, including computers and software packages designed to at least partially operate independent of a data network and in which various steps of the currently described methods can be accomplished in an automated fashion at a remote location (e.g., practitioner's office).

Figure 3C:
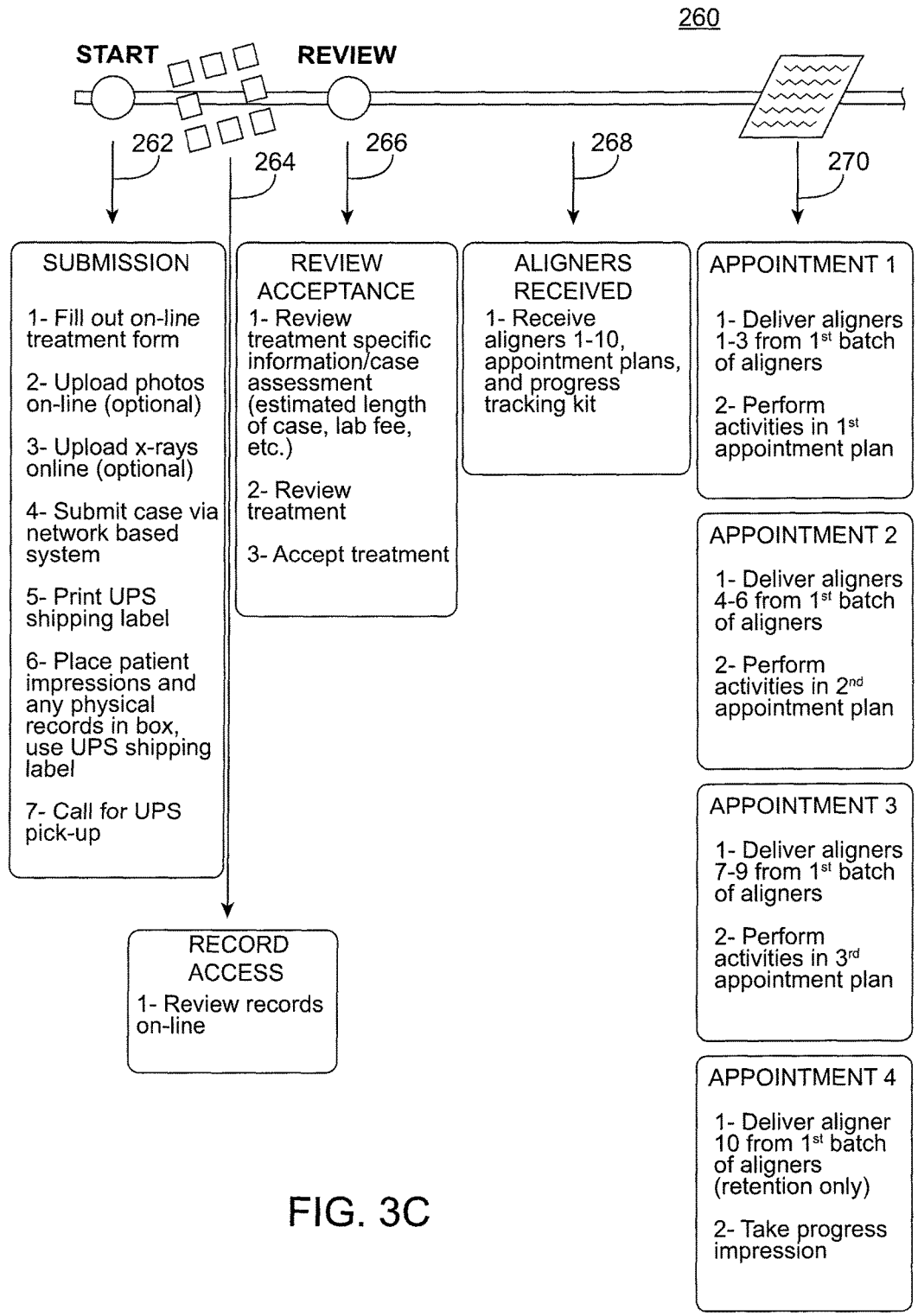
FIG. 3C is a diagram of a process according to an embodiment of the present invention.
Figure 3C:
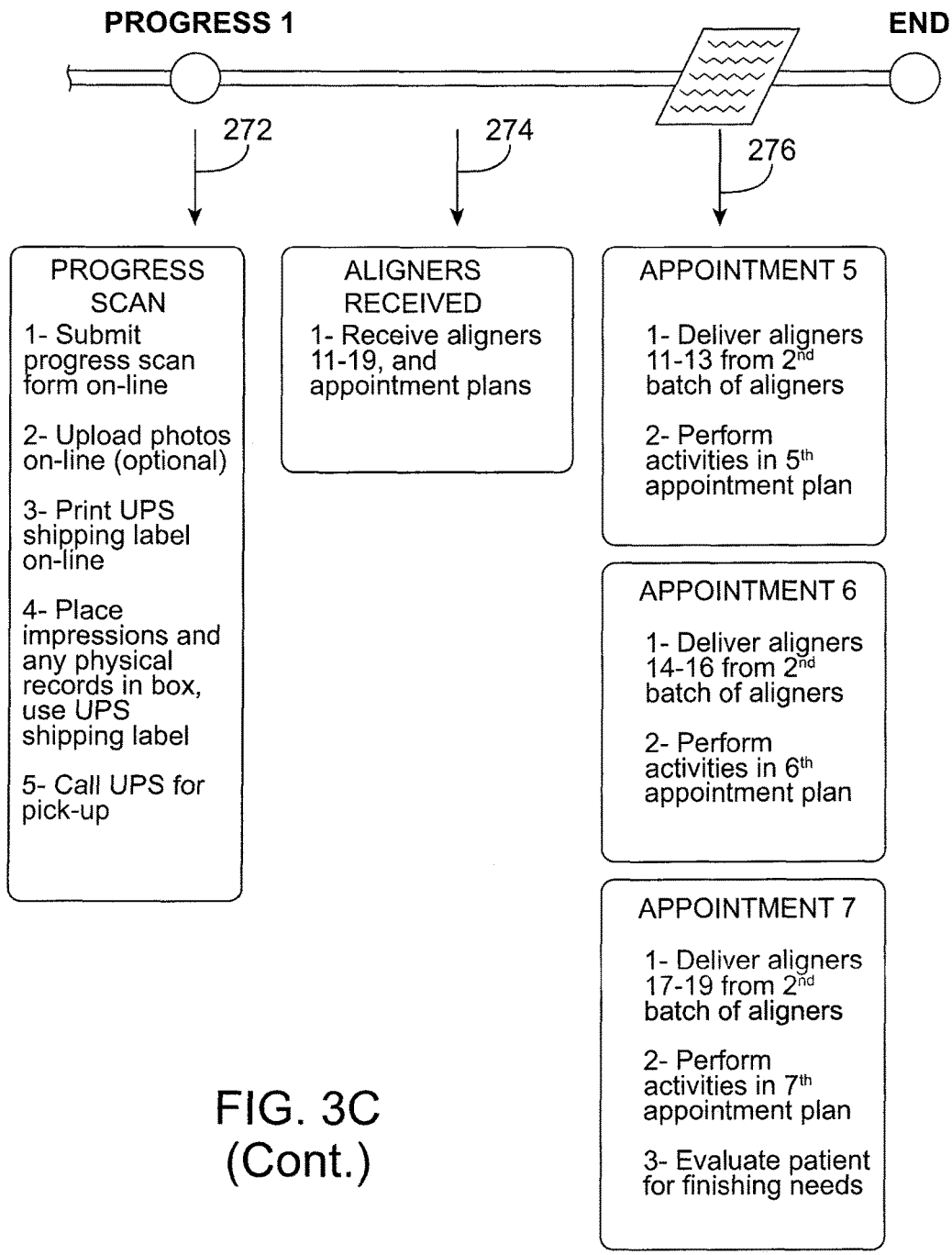

FIG. 3C is a flow diagram illustrating a process according to one embodiment of the present invention. The process 260 includes a series of steps according to an overall treatment of a patient. The process 260 includes submitting information regarding the patient and can include information indicative a dental condition of the patient and/or one or more treatment goals (Step 262). The information can be submitted via a network based system and can include directions, forms or other guidance for providing information to a third party (e.g., treatment planning party, appliance designer/manufacturer, etc.). Information can be stored in a database that can optionally be accessible for review (e.g., by the practitioner) (Step 264). Next, information submitted can be reviewed by a third party for case assessment and a treatment plan generated, which can be reviewed by the treating practitioner or patient, for example, and accepted or modified (Step 266). Appliances are then generated and provided to the practitioner, and are provided together with customized appointment planning tools/guidelines, and one or more kits for progress tracking (Step 268). Treatment according to the treatment plan is then administered to the patient in a series of one or more treatment phases, with each phase including a set of appliances and corresponding customized appointment and treatment guidelines (Step 270). Treatment progress tracking can be performed to determine whether treatment is progressing as planned and can include, for example, submitting (e.g., electronic transmission, shipping, etc.) progress information such as treatment notes and observations, scans, photos, impressions, and the like for progress tracking analysis (Step 272). A next batch of appliances can be sent to the practitioner (Step 274) and, depending on the results of the progress tracking analysis, can be the next set of appliances in the original treatment phase or can be provided according to a revised treatment phase. Treatment according to the next phase of the plan, including the appliances received in Step 274, is then administered to the patient (Step 276). Treatment then either progresses to the final stages of treatment if the desired position of the teeth is achieved or treatment progresses according to a treatment plan.

Figure 4:
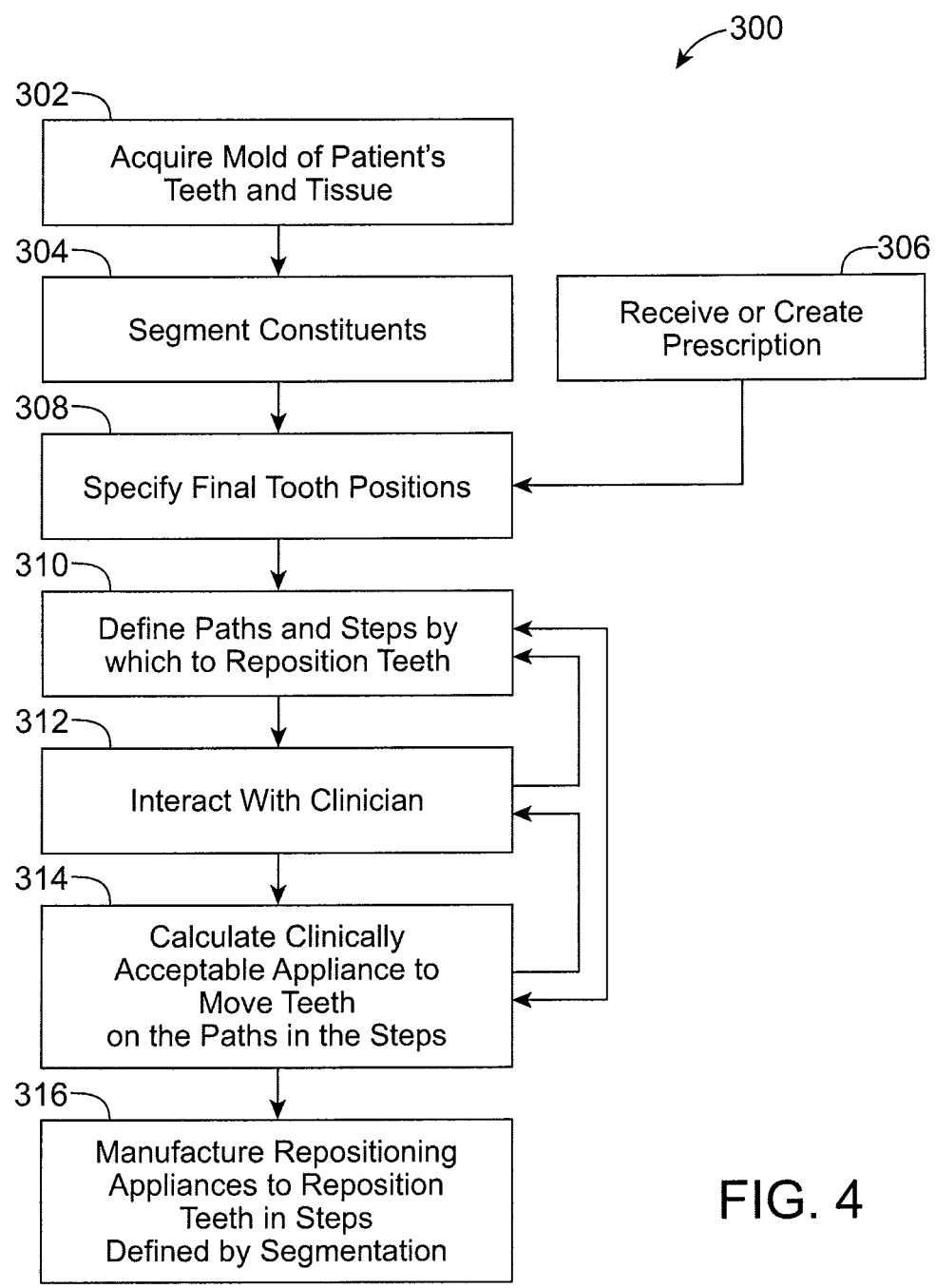
FIG. 4 illustrates generating a treatment plan according to an embodiment of the present invention.

FIG. 4 illustrates the general flow of an exemplary process 300 for defining and generating a treatment plan, including repositioning appliances for orthodontic treatment of a patient. The process 300 includes the methods, and is suitable for the apparatus, of the present invention, as will be described. The steps of the process can be implemented as computer program modules for execution on one or more computer systems.

As an initial step, a mold or a scan of patient's teeth or mouth tissue is acquired (Step 302). This generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents an initial (e.g., pretreatment) arrangement of the patient's teeth and other tissues.

The initial digital data set, which may include both raw data from scanning operations and data representing surface models derived from the raw data, is processed to segment the tissue constituents from each other (Step 304), including defining discrete dental objects. For example, data structures that digitally represent individual and/or sections of tooth crowns can be produced. In some embodiments, digital models of entire teeth are produced, including measured or extrapolated hidden surfaces and root structures.

Desired final position of the teeth, or tooth positions that are desired and/or intended end result of orthodontic treatment, can be received, e.g., from a clinician in the form of a descriptive prescription, can be calculated using basic orthodontic prescriptions (e.g. Roth, Andrews, Ricketts, etc.), or can be extrapolated computationally from a clinical prescription (Step 306). With a specification of the desired final positions of the teeth and a digital representation of the teeth themselves, the final position and surface geometry of each tooth can be specified (Step 308) to form a complete model of the teeth at the desired end of treatment. The result of this step is a set of digital data structures that represents a desired and/or orthodontically correct repositioning of the modeled teeth relative to presumed-stable tissue. The teeth and surrounding tissue are both represented as digital data.

Having both a beginning position and a final target position for each tooth, the process next defines a treatment path or tooth path for the motion of each tooth (Step 310). This includes defining a plurality of planned successive tooth arrangements for moving teeth along a treatment path from an initial arrangement to a selected final arrangement. In one embodiment, the tooth paths are optimized in the aggregate so that the teeth are moved in the most efficient and clinically acceptable fashion to bring the teeth from their initial positions to their desired final positions.

At various stages of the process, the process can include interaction with a clinician responsible for the treatment of the patient (Step 312). Clinician interaction can be implemented using a client process programmed to receive tooth positions and models, as well as path information from a server computer or process in which other steps of process 300 are implemented. The client process is advantageously programmed to allow the clinician to display an animation of the positions and paths and to allow the clinician to reset the final positions of one or more of the teeth and to specify constraints to be applied to the segmented paths.

The tooth paths and associated tooth position data are used to calculate clinically acceptable appliance configurations (or successive changes in appliance configuration) that will move the teeth on the defined treatment path in the steps specified (Step 314). Each appliance configuration corresponds to a planned successive arrangement of the teeth, and represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically acceptable amount of force on the patient's dentition. As with other steps, this calculation step can include interactions with the clinician (Step 312).

Having calculated appliance definitions, the process 300 can proceed to the manufacturing step (Step 316) in which appliances defined by the process are manufactured, or electronic or printed information is produced that can be used by a manual or automated process to define appliance configurations or changes to appliance configurations. Appliances according to the treatment plan can be produced in entirety, such that each of the appliances are manufactured (e.g., prior to treatment), or can be manufactured in sets or batches. For example, in some cases in might be appropriate to manufacture an initial set of appliances at the outset of treatment with the intention of manufacturing additional sets of appliances (e.g., second, third, fourth, etc.) after treatment has begun (e.g., as discussed further herein). For example, a first set of appliances can be manufactured and administered to a patient. Following administration, it may be desirable to track the progression of the patient's teeth along the treatment path before manufacturing and/or administering subsequent set(s) of appliances.

Generating and/or analyzing digital treatment plans, as discussed herein, can include, for example, use of 3-dimensional orthodontic treatment planning tools such as ClinCheck from Align Technology, Inc. or other software available from eModels and OrthoCAD, among others. These technologies allow the clinician to use the actual patient's dentition as a starting point for customizing the treatment plan. The ClinCheck technology uses a patient-specific digital model to plot a treatment plan, and then uses a processed (e.g., segmented) scan of the achieved treatment outcome to assess the degree of success of the outcome as compared to the original digital treatment plan as, as discussed in U.S. Pat. Nos. 7,156,661 and 7,077,647 (see also, below).

Case Assessment

As set forth above, a case assessment can be generated so as to characterize the desired or appropriate treatment, including assessing or characterizing the complexity or difficulty in achieving a given treatment, or conducting a preliminary analysis of the treatment parameters (e.g., goals) for a determination of certain treatment options that may be desired or available (e.g., customized guidelines, progress tracking features, etc.). Users can receive information to determine whether a patient's orthodontic conditions qualify for a particular treatment and further can obtain information associated with the treatment such as treatment difficulty, the level of skills necessary or recommended to perform the proposed treatment, anticipated treatment duration period, associated costs, and the like. In one embodiment, the assessment can include generating a manual visual aid or a computerized visual guide interface system. Additionally, in the computerized visual guide interface system, there are provided one or more databases which have stored therein an index of statistical information, computational algorithms, patient conditions, and associated treatment information based upon, for example, desired one or more treatment goals. Further description of certain assessment systems and methods, including case difficulty assessments, see, for example, commonly owned U.S. application Ser. No. 11/580,536, entitled "Method and System for Providing Dynamic Orthodontic Assessment and Treatment Profiles," filed on Oct. 13, 2006, which is incorporated herein by reference.

The assessment process generally involves receiving information regarding the patient's orthodontic condition and/or treatment history, processing the received information including, e.g., using consultation or opinion (e.g., expert opinion), computational algorithms, clinical data and statistics, and/or historical case content, and the like, and transmitting results of the assessment to a user of the system (e.g., practitioner, clinician, patient, etc.). In this manner, a preliminary determination can be made whether a patient's orthodontic conditions and/or the identified treatment goals qualify for treatment using certain appliances (e.g., Invisalign® System) generally, or more specifically qualification a particular treatment package including pre-selected treatment options. In some instances, an assessment can include simply receiving a practitioner's selection of desired enhanced treatment plan options (e.g., appointment planning tools, progress tracking features, etc.). In addition, based on information received a determination can be made regarding treatment parameters including approximate number of aligners necessary, approximate treatment duration, difficulty of the treatment, associated level of real or perceived pain related to the treatment, and any other relevant characteristics or parameters that would be useful to the user of the system. Case assessment can occur at various points in a process according to the present invention, but will typically occur following receiving patient/treatment information and can occur before or after generating an initial treatment plan.

FIG. 5 is an example user interface display for illustrating case assessment information in accordance with one embodiment of the present invention. The user interface display 350 includes information for a particular patient's orthodontic treatment as determined by the patient's initial conditions and the desired or selected treatment goals and/or options. The user interface 350 in one embodiment is configured to display a simplified view of a treatment plan 352, and can provide a general treatment timeline showing certain treatment options, such as appointment planning tools and progress tracking. Displayed treatment options can be interactive such that selection of a particular option in the treatment plan view 352 generates more detailed display of steps or tasks in the selected option. The display 350 can further include information 354 regarding the case assessment including, e.g., qualification for a particular treatment service package, estimated costs and duration, as well as links for more detailed appointment planning tools. The display 350 can further include information 356 or options to modify treatment goals or a treatment plan, or option 358 to accept and proceed with the proposed treatment plan.

Appointment Planning

As set forth above, once a treatment plan is in place the present invention includes generating customized treatment guidelines that can be provided to the dental practitioner for facilitating administration of treatment and improving desired treatment outcomes. Since the treatment plan typically includes a series of one or more treatment phases, a customized set of treatment guidelines will be generated and will typically include a set of guidelines corresponding to each phase of the treatment plan. Treatment guidelines are provided to the practitioner for administration of treatment to the patient. Since a phase(s) of treatment can include a set of appliances to be administered to the patient, treatment guidelines can be provided to the practitioner concurrently with a set of appliances, or appliances and guidelines can be provided separately. Guidelines can include, for example, hard copies (e.g., paper copies) printed and shipped to the practitioner, or can include one or more electronic copies transmitted to the practitioner over a network, for example, by email or by incorporation into other network-based treatment planning tools (e.g., ClinCheck®).

As a treatment plan will typically include a series of one or more appointments, guidelines will typically include one or more recommended patient/practitioner appointments that may include suggested timing for the appointments. Suggested timing can be specific and may more particularly identify a date or specific date range for scheduling one or more appointments, or can be more generalized and for each appointment may list a broader timing range (e.g., 1 week appointment, 2 week, 3 week, etc.). Appointment timing can be identified to coincide with another treatment event, such as administering an appliance or set of appliance, or wearing of an appliance(s) by the patient for a period of time. Guidelines corresponding to a particular appointment can include a list of recommended tasks to be completed during the practitioner's appointment with the patient. Non-exclusive examples of general tasks that may need to be performed at a given appointment can include appliance delivery and administration to the patient; tooth modifications such as extractions, interproximal reduction (IPR), periodontal evaluation, and the like; placement/removal of attachment(s); auxiliary placement; general monitoring and compliance; treatment progress tracking; finishing appointment or finalization of treatment (e.g., refinement evaluation or final impression and/or order retainer); retainer administration to the patient; retainer maintenance; cleaning appointments; etc. Since the guidelines provided to the practitioner will be specifically customized to the individual patient, the guidelines will not only include identification of the tasks to be completed but will typically include specific details and/or instructions, customized to the individual patient, that will help guide the practitioner through the identified tasks during an appointment with the patient. In some instances, the information provided in the customized guidelines can be further tailored to the practitioner to provide the appropriate level of detail, content, and the like. For example, information provided to the practitioner, such as amount of detail in the identified tasks, can be selected based on the experience level of the practitioner or preferences of the practitioner, e.g., including preferences specified by the practitioner.

As set forth above, guidelines can include, for example, hard copies (e.g., paper copies) printed and shipped to the practitioner, or can include one or more electronic copies transmitted to the practitioner over a network. In addition to recommended appointments, recommended tasks, and specific instructions or guidance on how tasks may be completed, guidelines according to the present invention can include additional information and/or details that can further facilitate a practitioner in administering treatment to the patient, such as support contact information, direction to additional training materials, product ordering information, and the like. For example, where guidelines are provided electronically, such as on-line, additional materials can include one or more hyperlinks, such as JIT troubleshooting links, support links and/or numbers, e-mail links, order placement links, links to ClinCheck® sharing modules, training modules or information, etc.

Figure 6:
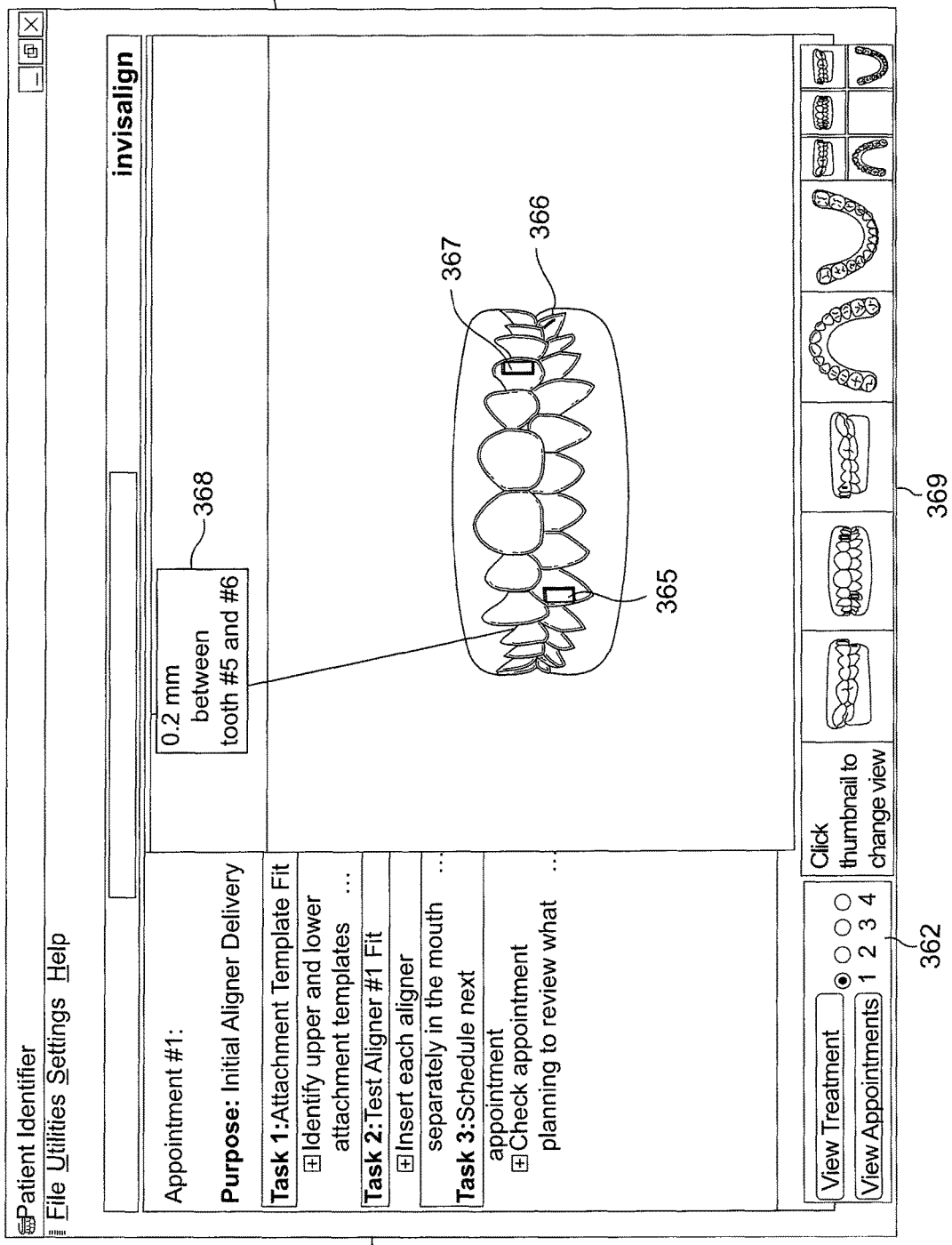
FIG. 6 illustrates a user interface graphical representation of electronically provided guidelines corresponding to a treatment plan according to an embodiment of the present invention.

FIG. 6 shows a screen shot including a user interface 360 illustrating a graphical representation of electronically provided guidelines corresponding to a treatment plan according to an embodiment of the present invention. A user can select a given appointment (example "Appointment #1" is illustrated) from an appointment menu 362 and customized set of treatment guidelines 364 are displayed corresponding to the selected appointment. The guidelines 364 can include a general description of the selected appointment (e.g., "purpose") so as to communicate to the practitioner general goals to be accomplished at the appointment. The guidelines 364 can further include a list of specific tasks to be completed. Specific tasks can be selected by the practitioner for further viewing of more specific details, such as by selecting a drop down menu that provides more detailed and specific instructions to guide the practitioner through administration of the tasks. For a given appointment, a graphical representation of the patient's projected tooth position 366 at a given appointment or time can be provided and incorporated into the interface for delivering the guidelines or task instructions. For example, as shown, specific identification 368 of interproximal reduction areas may be shown and can contain details on the reduction to be performed. Attachment locations 365, 367 can also be illustrated on the representation 366 to facilitate treatment administration. Additional views 369 (e.g., thumbnail views) of the patients teeth can also be provided for selection by the practitioner. Providing the guidelines and instructions along with such graphical illustrations can advantageously help to more effectively communicate task instructions to the practitioner at the appropriate point in the treatment and more effectively manage treatment.

Figure 7A:
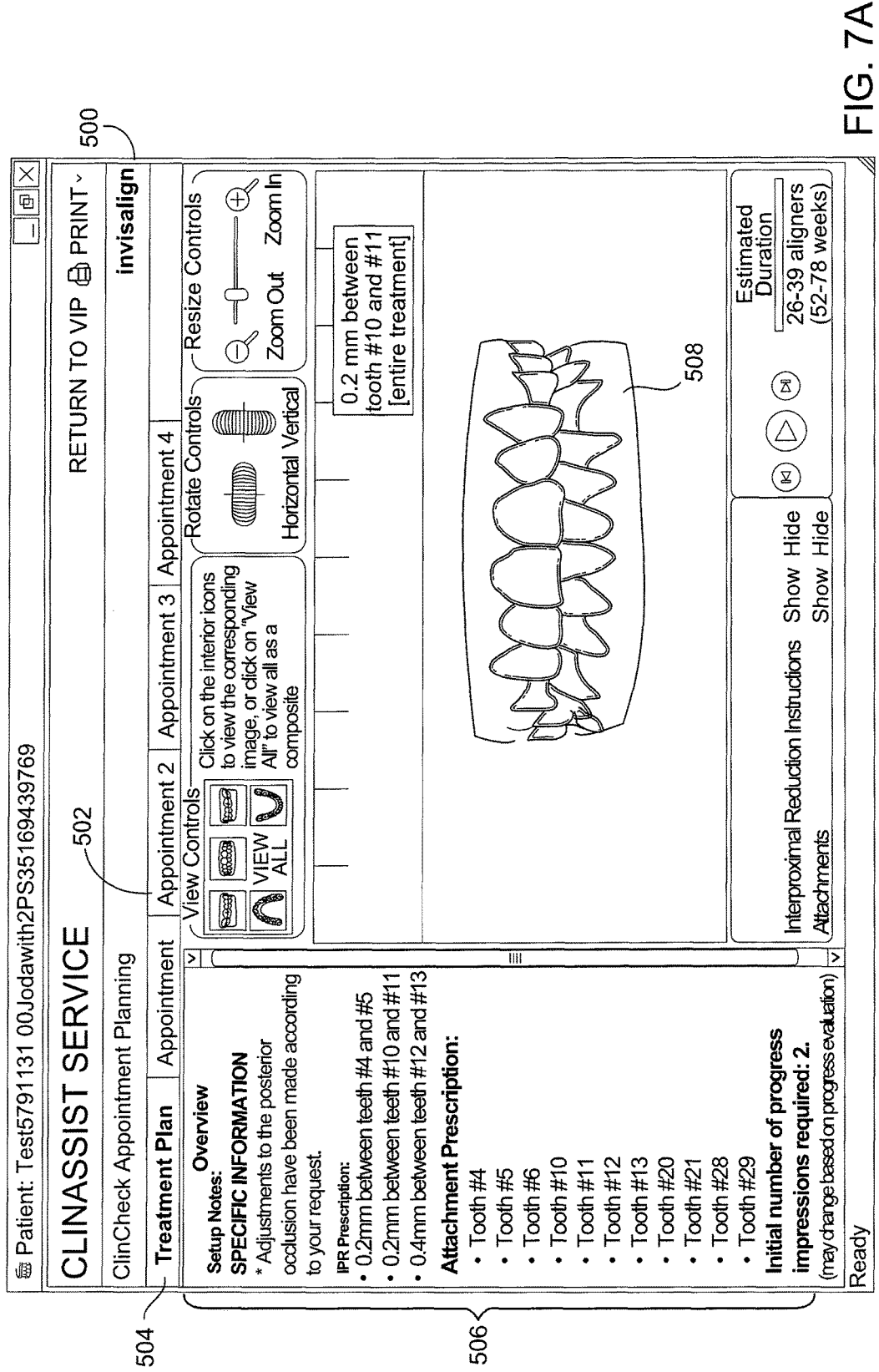
FIG. 7A illustrates a user interface graphical representation of electronically provided guidelines according to another embodiment of the present invention.

FIG. 7A shows a screen shot 500 illustrating a graphical representation of electronically provided guidelines according to another embodiment of the present invention. As above, a user can select a given appointment (e.g., "Appointment 1", "Appointment 2", etc.) from an appointment menu 502 (e.g., appointment menu bar) for viewing of information including customized guidelines corresponding to the selected appointment. Additionally, the appointment menu 502 can include an option to select an overview or general information on the treatment plan in general, which can be graphically represented as a treatment plan overview tab 504 in the menu 502. Selection of the overview 504 can further display overview information 506 providing information on the treatment plan in general. Information 506 can include, for example, a list of tasks to be completed throughout the treatment (or portion thereof) of the patient. Specifically identified task may be linked to other files so as to provide additional detailed information on a given task upon selection. As above, a graphical representation 508 of the patient's teeth can be presented illustrating projected tooth positions at a given time or appointment.

Figure 7B:
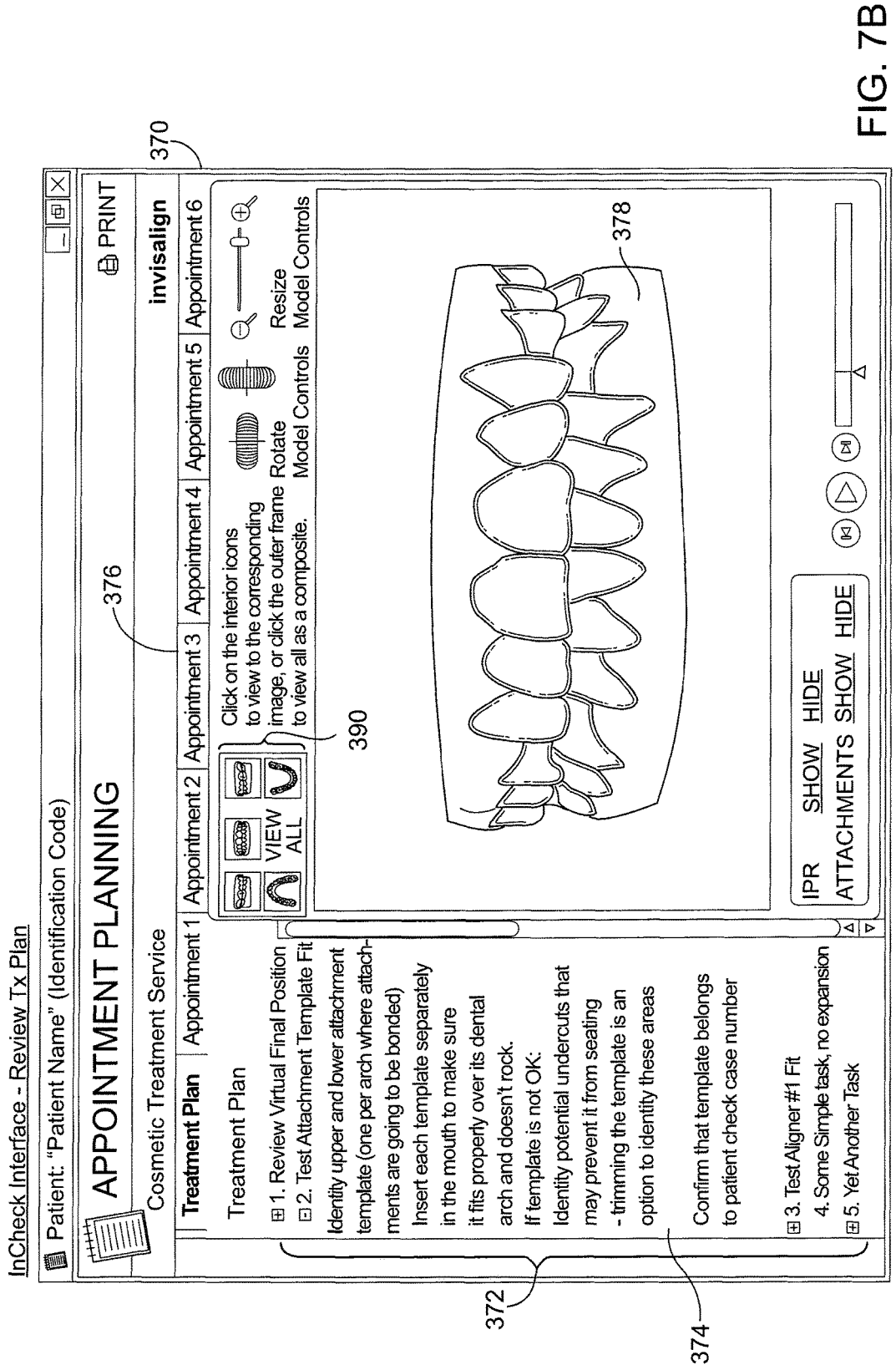
FIG. 7B illustrates a user interface graphical representation of electronically provided guidelines corresponding to a treatment plan according to another embodiment of the present invention.

FIG. 7B shows a user interface 370 illustrating a graphical representation of electronically provided guidelines corresponding to a treatment plan according to another embodiment of the present invention. Customized treatment guidelines 372 are shown provided according to the treatment plan. As above, drop down options 374 are provided that allow the practitioner to select a given task in order to view more detailed instructions and information for guidance on how to administer the task. The practitioner can toggle between various appointments by using an appointment menu 376 (e.g., menu bar), where a given appointment according to the treatment plan can be selected, thereby providing a list of corresponding tasks to be completed at the selected appointment. Additionally, a graphical representation 378 of the patient's projected tooth positions at the given time or appointment can be displayed and may include a view menu 390 for selecting different graphical views of the patients teeth. Additional animation and/or instructions can be included or incorporated into a graphical representation of the patient's teeth to further communicate treatment guidelines and tasks.

Progress Tracking

In some cases, patients do not progress through treatment as expected and/or planned and, therefore, tracking or monitoring the progress of the patient's treatment will be desired. For example, in some instances a patient's progression along a treatment path can become "off-track" or will deviate from an initial treatment plan, whereby an actual tooth arrangement achieved by the patient will differ from the expected or planned tooth arrangement, such as a planned tooth arrangement corresponding to the shape of a particular appliance. A determination that the progression of a patient's teeth is deviating or not tracking with the original treatment plan can be accomplished in a variety of ways. As set forth above, off-track deviations can be detected by visual and/or clinical inspection of the patient's teeth. For example, a substantial off track deviation from the expected or planned treatment may become apparent when the patient tries to wear a next appliance in a series. If the actual tooth arrangement substantially differs from the planned arrangement of the teeth, the next appliance will typically not be able to seat properly over the patient's teeth. Thus, an off-track deviation may become substantially visually apparent to a treating professional, or even to the patient, upon visual or clinical inspection of the teeth.

Detecting deviations from a planned treatment, however, can be difficult, particularly for patients as well as certain dental practitioners, such as those with more limited experience in orthodontics, certain general dentist, technicians and the like. Additionally, deviations that have progressed to the point that they are visually detectable clinically are often substantially off track with respect to the planned treatment, and earlier means of off-track detection is often desired. Thus, detecting deviations from a treatment plan can also be accomplished by comparing digital models of the patients teeth, and can often detect deviations from a treatment plan before the deviation becomes substantially apparent by visual or clinical inspection.

Methods and techniques for tracking and preserving the original final position in the treatment is generally referred to herein as "teeth matching" or "bite matching". For example, bite matching techniques described herein can include matching teeth from the original image of the teeth or impression, to surface(s) of a new model of the teeth taken after treatment has begun. An off-track determination can be followed by "re-setting" to the actual position of the teeth as defined by data represented in the progress scan, the original data of the teeth (i.e., segmented models from initial treatment plan), thereby allowing preservation of the initially selected final target position of the teeth. In other words, the original data set which contains with it, an established target arrangement, can be reused, by repositioning the teeth arrangement according to the positions of the (same) teeth captured in the progress scan. In so doing, a new planned path to go from the current to the target can be recreated without having to change the original target configuration. This method includes using bite matching techniques to allow the current aligner geometry to be recalibrated and reshaped according to the actual position of the teeth in the progress scan. Using such bite matching techniques provides significant advantages in terms of efficiency as there is no need to re-segment and process the new scan of the teeth, and in terms of efficacy since the initial final arrangement is preserved, even if the patient progresses off track.

Incorporating the inventive techniques and tracking methods described herein in managing delivery/modification would provide various advantages, including earlier detection of treatment deviations, allowing earlier remedial measures to be taken, if necessary, to avoid undesirable treatment outcomes and preservation of initial treatment goals, thereby ultimately allowing for more effective treatment and better clinical outcomes. Furthermore, treatment efficiency and efficacy can be increased by better avoidance of inefficient/undesirable treatment "detours". Additionally, improved monitoring and tracking, as described, is more objective and reliable, and less qualitative in nature than the common practice of visually identifying off-track progress. As such, currently described inventive methods and techniques can inspire more confidence in both patients and practitioners, including practitioners (e.g., general dentist) that may be less experienced with a given treatment method and/or less confident in their abilities to clinically detect off-track progression, or more experienced practitioners who may desire more detailed monitoring, for example, in cases involving more difficult or less predictable movements.

Figure 8:
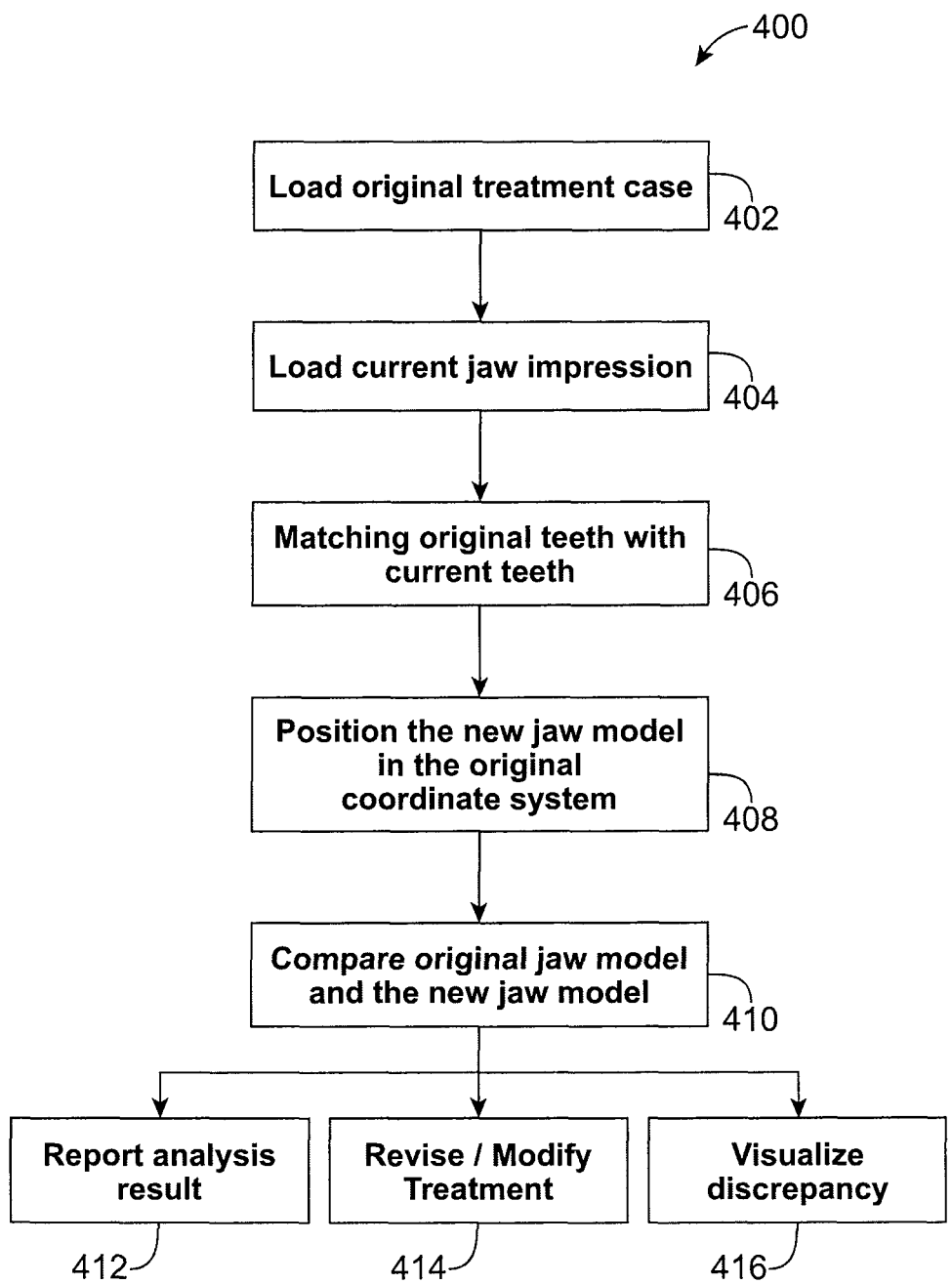
FIG. 8 illustrates a process including teeth matching according to one embodiment of the present invention.

An exemplary computer based teeth matching process according to an embodiment of the present invention is described with reference to FIG. 8. First, data from an earlier treatment plan is received (Step 402). Typically, data includes the initial data set or image data representing the patient's teeth in the original, pre-treatment positions, the initially identified final position, as well as planned intermediate or successive arrangements selected for moving teeth along the initial treatment path from the initial arrangement to the selected final arrangement. Next, a current jaw impression or data including a digital representation of the teeth in their current positions, after treatment has begun, is received and loaded (Step 404). Data including planned arrangements of the teeth are then compared to data including a representation of the patient's teeth in their current positions for an initial determination of whether a match exists (Step 406). Next, the new jaw data is segmented and positioned in the original coordinate system (Step 408). The process then compares the original jaw data against the new jaw data (Step 410). Based on the comparison, the process generates an analysis report (Step 412), new/revised treatment options or plans (Step 414), and/or allows visualization of any detected discrepancy (Step 416). See also, e.g., U.S. Pat. Nos. 7,156,661 and 7,077,647, for discussion of comparing actual position of the teeth relative to a planned or expected position using a processed (e.g., segmented) scan of the teeth positions following initiation of treatment.

In some instances, detecting a deviation from a treatment plan via comparison between digital models of the patients teeth can include comparing a current scan or image, which has not been segmented, of the patients teeth in a position after treatment has begun to a previously segmented data set of the patients teeth at a current, past or future stage. Use of an unsegmented, rather than segmented, digital representation of the current teeth positions may be desirable, for example, in order to avoid resource and/or labor intensive processing steps to transform the current unsegmented digital teeth model to a segmented digital teeth model. In addition, lower resolution or quality scans or images can save cost and time if the necessary reference points can be identified on the unsegmented current scan or image.

Figure 9:
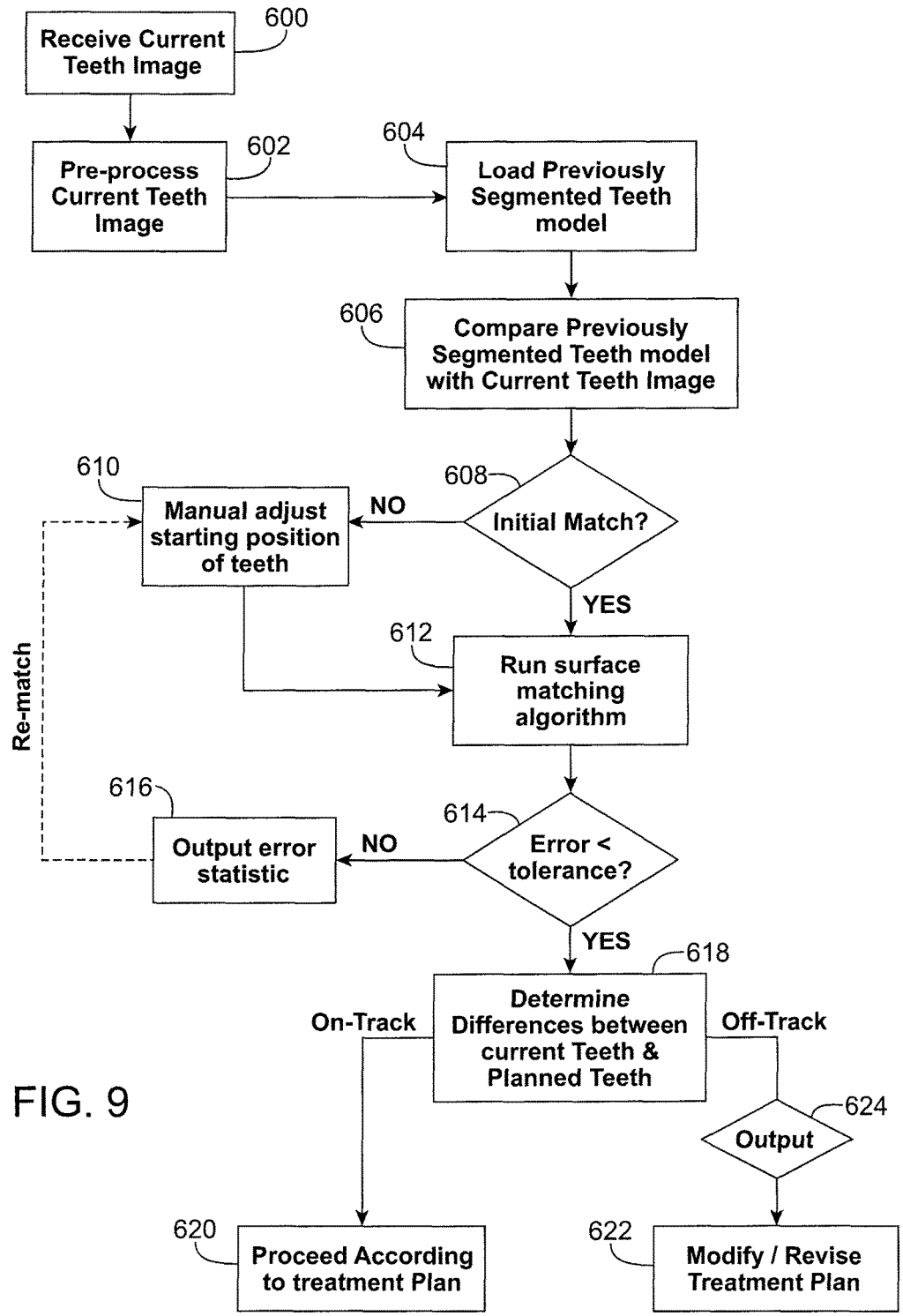
FIG. 9 shows a process including teeth matching according to another embodiment of the present invention.

FIG. 9 is a flow chart showing the steps of correcting deviations from a planned course of treatment to gradually reposition teeth, according to one embodiment of the present disclosure. The process starts in step 600, when current jaw data or "Current Teeth Image" is received. The current jaw data includes data representing an actual arrangement of the patients teeth following administration of appliances according to the original treatment plan. In step 602, the Current Teeth Image is pre-processed using a digital data tool (DDT) such that each tooth is assigned a Facial Axis of the Clinical Crown (FACC), i.e. a unique current identifier, with jaw characteristics set. Typically, according to the described embodiment, the Current Teeth Image does not need to be segmented, which saves a technician's time and hence overall cost.

In step 604, a Previously Segmented Teeth Model is selected, and is input into a system of the present invention for analysis and comparison with the Current Teeth Image. The Previously Segmented Teeth Model selected can include an Initially Segmented Teeth Model or a digital model of the patient's teeth in their initial, pre-treatment positions, the initial final position according to the initial or previous treatment plan (e.g., Prescribed Tooth Arrangement), or a planned successive tooth arrangement therebetween.

In step 606, the Previously Segmented Teeth Model and the Current Teeth Image are compared. This step includes a sort of "rough match" of the segmented model and the Current Teeth Image to identify corresponding features of the two models that may be compared (Step 608). For example, an initial matching algorithm can be executed which matches unique starting identifiers (FACCs) of each tooth in the Previously Segmented Teeth Model to the respective unique current identifiers (FACCs) of each tooth in the Current Teeth Image. The images can be overlaid on each other and the relative location of each tooth identified by its unique identifier (or FACC) to determine if there are any mismatches in step 608.

If any mismatches are found, an initial match has not occurred and the mismatches are displayed in the form of an informational dialog that provides details of the mismatches, such as teeth numbering irregularities or missing FACCs. A mismatch can occur, for example, if there are any teeth numbering irregularities, such as the total number of teeth in each model is not the same, or at least one tooth is missing a FACC. Mismatches may result, for example, where substantial dental work or reconstruction (e.g., tooth extraction, tooth reconstruction, filling, etc.) has occurred following the initial treatment plan or generation of Previously Segmented Teeth Model.

In Step 610, initial mismatch errors as identified above can be manually accounted for in the process. For example, a technician can manually adjust or reposition each tooth with a mismatch using the Previously Segmented Teeth Model or adjusts the information relating to each tooth with a mismatch (e.g., accounting for an extracted tooth).

If no mismatches are generated in step 608, or where mismatches have been accounted for according to 610, then an initial match occurs and the process moves to step 612. The initial match confirms that the technician is using the correct Previously Segmented Teeth Model and the Current Teeth Image, which provides a good starting point for executing a surface matching algorithm.

In step 612, more detailed matching and comparison between Previously Segmented Teeth Model and the Current Teeth Image occurs, which includes execution a surface matching algorithm. The surface matching algorithm can take a number of samples of each tooth in the Previously Segmented Teeth Model and finds the closest corresponding sampling point on the Current Teeth Image. A grid is created on each tooth and the number of samples is randomly selected and then the grid is overlaid on the Current Teeth Image.

In step 614, any resulting errors from the surface matching algorithm are compared to predetermined tolerances to determine if the resulting errors are less than the predetermined tolerance. Error tolerances can account for potential differences in the models being compared that might impair meaningful comparison, such as errors due to typical variance between different scans or impressions, surface differences or fluctuations, and the like. If the resulting errors are greater than the pre-determined tolerance, then in step 616, error statistics for the surface matching algorithm are typically output to a display device and can be further redirected to a technician for manual input or correction as in step 610.

If the resulting errors are less than the pre-determined tolerance, in step 618, then matching and comparison of the Previously Segmented Teeth Model and the Current Teeth Image proceeds for a determination whether the actual arrangement of the patient's teeth deviates from the planned arrangement. In particular, a determination can be made as to whether positional differences exist, and to what degree, between the teeth in their current positions compared to the expected or planned positions. Positional differences may indicate whether the patient's teeth are progressing according to the treatment plan or if the patient's teeth are substantially off track. Various clinical and/or positional parameters can be examined and compared for a determination as to whether a patient's teeth are substantially on track or are deviating from an expected arrangement according to the treatment plan. For example, positional parameters examined can include tooth rotation, extrusion, intrusion, angulation, inclination, and translation. Threshold values for differences in one or more positional parameters can be selected as being indicative of a significant or substantial difference in tooth position. Exemplary threshold values for various positional parameters, according to one embodiment of the invention are listed in Table 1 below. Detecting positional differences above the selected threshold value(s) indicates that the actual arrangement of the patients teeth substantially deviates from the planned arrangement to which the comparison is made.

TABLE 1

OFF TRACK DEFINITION. The threshold difference values of a planned position of teeth to actual positions selected as indicating that a patient's teeth have progressed substantially off-track.

| Type Movement | Difference Actual/Planned |
|---|---|
| Rotations | |
| Upper central incisors | 9 deg |
| Upper lateral incisors | 11 deg |
| Lower incisors | 11 deg |
| Upper cuspids | 11 deg |
| Lower cuspids | 9.25 deg |
| Upper Bicuspids | 7.25 deg |
| Lower First Bicuspid | 7.25 deg |
| Lower Second Bicuspid | 7.25 deg |
| molars | 6 deg |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 deg |
| Posterior | 3.7 deg |
| Inclination | |
| Anterior | 5.5 deg |
| Posterior | 3.7 deg |
| Translation | |
| BL Anterior | 0.7 mm |
| BL Posterior Cuspids | 0.9 mm |
| MD Anterior | 0.45 mm |
| MD Cuspids | 0.45 mm |
| MD Posterior | 0.5 mm |

If the patient's teeth are determined to be on track by comparison of the teeth in their current positions with teeth in their expected or planned positions, then treatment can progress according to the existing or original treatment plan (Step 620). For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether the patient's teeth are progressing as planned or if the teeth are off track. If the patient's teeth are determined off track and deviating from the planned arrangement, then treatment according to the original treatment plan will be suspended. Typically, a modified or revised treatment plan will be generated where a patient's teeth are determined as being substantially off track (Step 622). Regardless of whether the patient's teeth are determined to be off track or progressing according to the treatment plan, the process can generate a report or analysis of the results, and/or visualize the comparison, including any detected discrepancy (Step 624). Any such product can be transmitted, for example, to a technician or treating professional, to the patient, or elsewhere.

Figure 10:
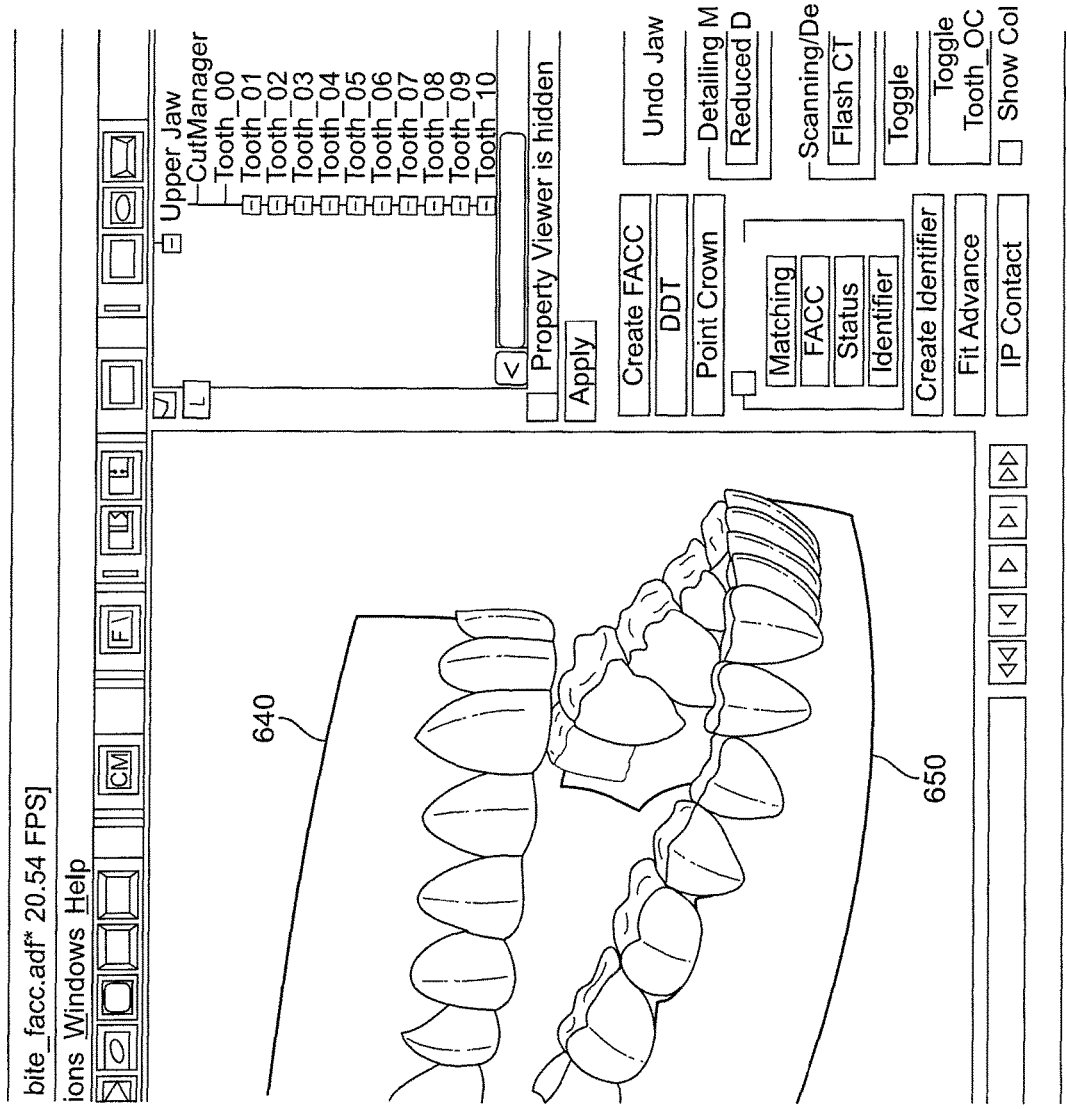
FIG. 10 is a screen shot showing a graphical representation of a three-dimensional model of a patient's upper and lower jaws based on a current digital data set representing teeth in their current positions, according to an embodiment of the present invention.

FIG. 10 is a screen shot showing a graphical representation of a three-dimensional model of a patient's upper and lower jaws 640, 650 generated from a Current Teeth Image. As described above, using a digital detailing tool (DDT), a technician pre-processes the Current Teeth Image by assigning and placing FACC's or unique current identifiers 74 on each tooth in the model. Unique current identifiers are landmarks on the teeth for the purposes of matching. Each FACC has a number associated with it and that is the tooth number, so the same tooth from the Previously Segmented Teeth Models and the Current Teeth Image should be in a similar location.

Figure 11:
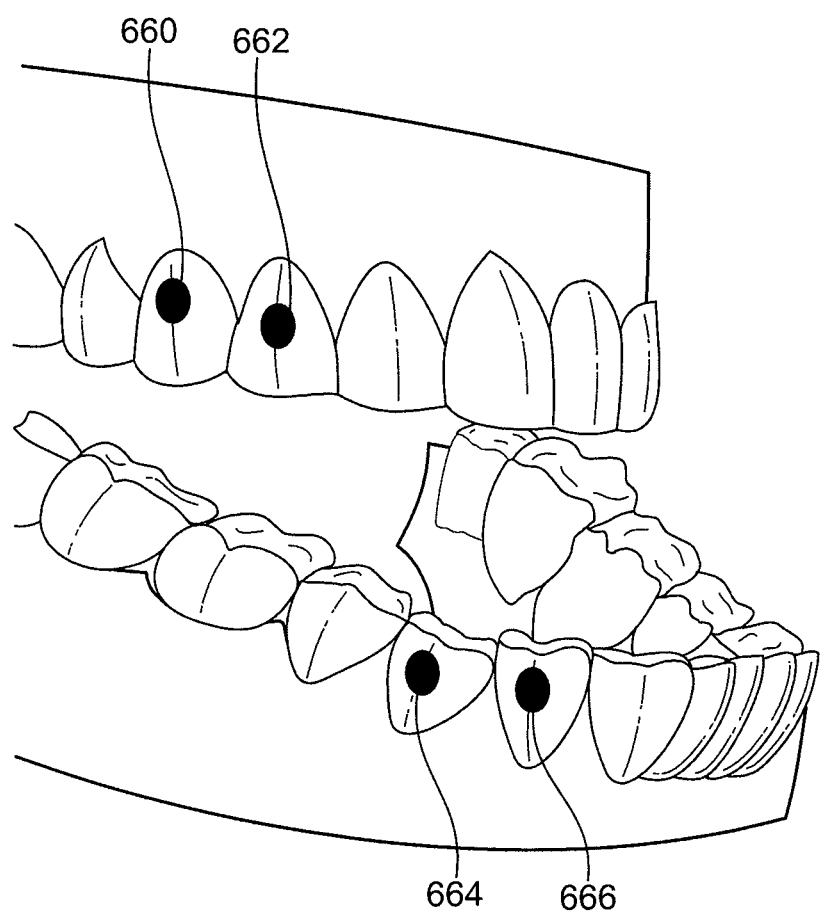
FIG. 11 is a graphical representation of a three-dimensional model of an initial match that can occur when the three dimensional model of digital translated images are overlaid on three dimensional model of the Current Teeth Image, according to one embodiment of the present invention.

FIG. 11 is a graphical representation of a three-dimensional model of a starting match that can occur when a Previously Segmented Teeth Model is overlaid on the Current Teeth Image, according to one embodiment of the present disclosure. The initial match provides a starting position for subsequent surface matching so that a good match is achieved.

If the initial matching algorithm determines that one or more teeth are mismatched, the initial matching algorithm cannot complete the initial matching satisfactorily because of teeth numbering irregularities or missing FACCs. In this instance, the initial matching algorithm will generate an informational dialog giving details of the mismatches allowing the technician to correct them and execute the initial matching algorithm again. Also shown in FIG. 8 are four attachments 660, 662, 664, 666 that have been optionally added to four of the patient's teeth.

See also, e.g., U.S. application Ser. No. 11/760,612, entitled "System and Method for Detecting Deviations During the Course of an Orthodontic Treatment to Gradually Reposition Teeth," filed on Jun. 8, 2007, the full disclosure of which is incorporated herein by reference, for further discussion of comparing an unsegmented representation of an actual arrangement of a patients teeth after treatment has begun, to a previously segmented model of the patient's teeth.

While the timing of the progress tracking steps described herein can be selected by the practitioner, typically at least general timing for conducting progress tracking measures of the present invention will be incorporated into the treatment plan and, therefore, will be pre-planned or planned at about the beginning of treatment or early on in the course of the patient's treatment (e.g., prior to the patient wearing a given set of appliances so as to reposition the teeth). Thus, in one embodiment of the invention, a treatment plan will include a prescribed timing for the planned tracking steps. The prescribed timing can include a specifically recommended date or may include an increment of time (e.g., at treatment week 9, 10, 11, etc.), or can be based on the timing of other events of the treatment plan (e.g., after a patient wears a set of appliances).

Timing of progress tracking steps can be selected to occur based on a somewhat standardized treatment protocol or can be more particularly customized to an individual patient. More standardized protocols can take into account certain population statistics, generalized clinical expectations, and/or physiological parameters that can be used to generally predict rate of movement of a patient's teeth and the minimum length of treatment time necessary for the patient's teeth to progress off track if such progression is occurring. Clinical parameters can include, for example, root structure, including length, shape, and positioning, as well as certain jaw characteristics such as jaw bone density, patient age, gender, ethnicity, medications/health history profile, dental history including prior treatment with orthodontics, type of orthodontic treatment plan (extraction vs. non-extraction), and the like. Assuming a 2-week wear interval for each appliance, with a maximum tooth velocity of 0.25 mm/tooth per aligner, typically about 16 to 20 weeks of repositioning treatment (8 to 10 appliances) is required before movement of the teeth is substantial enough to detect a non-compliant or off track movement of the teeth, if such off track movement is occurring, though more drastic movements can produce off track movement after only a few weeks.

As set forth above, timing of tracking measures can be selected based on the particular movement(s) prescribed and/or characteristics of the patient being treated and, therefore, are said to be customized to the particular patient. For example, certain desired tooth movements in a treatment plan may be deemed either more unpredictable or at increased risk of moving off track and may require specifically timed tracking or monitoring. Additionally, certain physiological or clinical characteristics of the patient may be identified as indicating that particularly timed and/or frequency of tracking might be desired. Whether tracking is selected based on standardized protocols or more customized to the individual patient, tracking may or may not be selected to uniformly timed during the course of treatment. For example, a lower frequency of tracking measures may be desired or needed during certain portions or phases of treatment than others (e.g. space closure). Regardless of whether tracking timing is customized or more standardized, the selected timing will typically provide the additional advantage of efficiently planning tracking in the treatment plan to minimize unnecessary use of practitioner time and other resources.

Figure 12A:
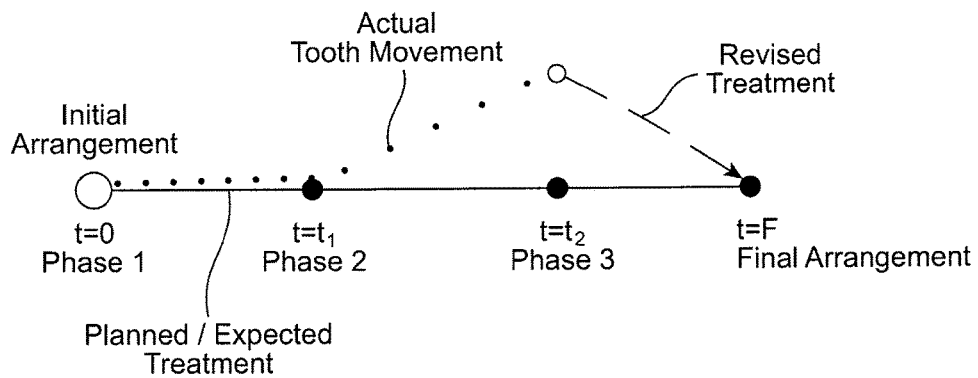
FIG. 12A through FIG. 12C show plurality of stages of teeth correction and revision of treatment, according to several embodiments of the present invention.
Figure 12B:
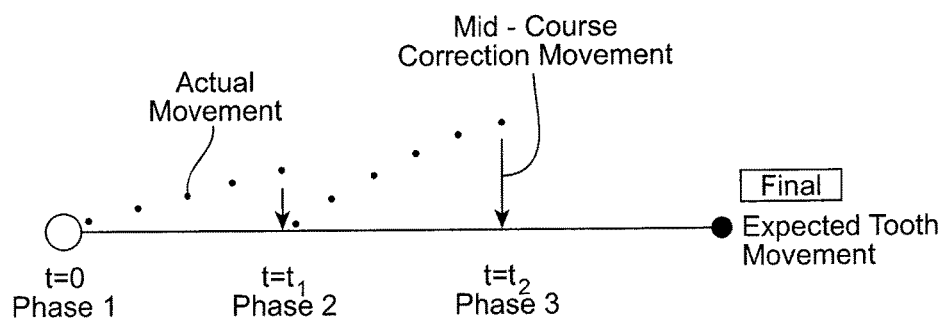
Figure 12C:
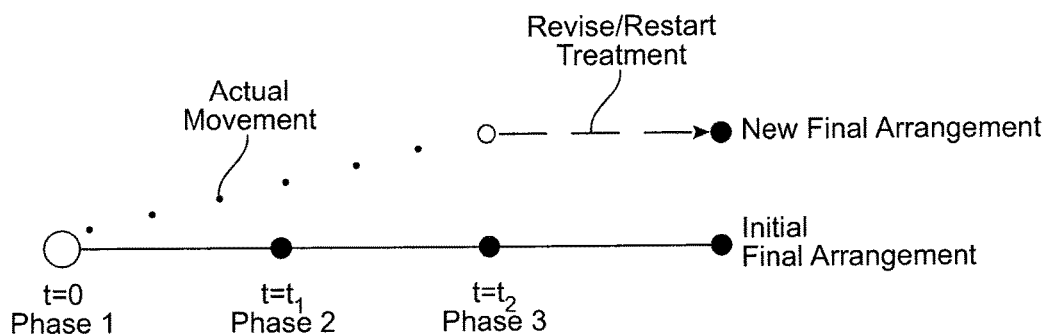

Once a determination is made that the patient's actual arrangement of teeth deviates from a planned arrangement and that the patient's teeth are not progressing as expected/planned, a change or correction in the course of treatment can be selected, for example, by generating an interim or modified treatment plan. Referring to FIGS. 12A-12C, revised treatment following determination that a patient's teeth are not progressing on track is described. As set forth above, a treatment plan includes a plurality of planned successive tooth arrangements for moving teeth along a treatment path from an initial arrangement to a selected final arrangement. The treatment plan, administration of sets of appliances to a patient according to the planned arrangements, can include a plurality of phases (1 through 4) where at time=0, the initial treatment plan begins. The initial treatment plan is illustrated by a solid line. Bite matching for a determination of whether a case is progressing "on track" or "off track", as described above (e.g., FIGS. 8, 9), can take place at one or more of the phases or points along the administration of treatment.

In particular, current tooth positions of the patient can be obtained from the patient any one or more phases and compared to segmented models of the patient's teeth according to an earlier or original treatment plan. Where teeth are determined to be deviating from the planned treatment plan or progressing "off track", as illustrated by broken lines, modification or revision of treatment plan can occur. In one embodiment, a revised treatment plan can include restaging the patient's treatment from the determined actual position to the originally determined final position (FIG. 12A). Revised treatment path (illustrated by dashed lines) can proceed directly toward the initially determined final position and need not attempt to redirect treatment back onto the original treatment path. In this case, while partial overlap/intersection of the revised treatment path with the original treatment path may occur, the revised treatment path will at least partially diverge from the initial treatment path and proceed directly toward the initially determined final arrangement of the teeth. Such an approach may be selected, for example, where retaining the initially determined final position is desired. This approach also advantageously permits use of the originally processed and segmented data, thereby allowing avoidance of costly processing steps.

Alternatively, a revised treatment plan can include a more direct "mid-course correction", in which the revised treatment plan includes a more direct path back toward the a planned arrangement of the initial treatment plan, as illustrated in FIG. 12B. While this approach may make use of the originally planned final arrangement, the more primary concern in this example type of correction is redirecting treatment back to the original treatment path, rather than from the actual position that is similar but not necessarily exactly the original final position. In yet another embodiment, as illustrated in FIG. 12C, a revised treatment plan can include essentially "re-starting" treatment, and generating a new final arrangement of the teeth, for example, from segmenting and staging a new impression of the teeth, and directing the patient's teeth from the actual arrangement to the newly determined final arrangement of the teeth.

Methodologies and systems of the present invention as described herein can include various techniques integrating and managing steps discussed above such as progress tracking into orthodontic treatment. For example, as new information is obtained during progress tracking measures, various data management techniques can be employed to make use of newly obtained data, manage existing data (e.g., data in initial treatment planning), and/or incorporate or seamlessly synchronize new information into treatment planning (e.g., revised treatment plan), staging of the teeth, system interface with treating professionals and/or patients, and the like. Thus, in one embodiment, the present invention can include synchronizing one or more aspects of a revised treatment plan so as to incorporate or integrate revised treatment with other aspects of treatment planning. For example, the revised treatment plan or data can be synchronized or integrated with expectations of a treating professional or patient for more seamless integration of new information and minimizing potential disruptions due to altered treatment.

In one embodiment, a treatment plan, initial or revised, can include a retention appliance or means to constrain for a period or hold in a desired or current position the patient's teeth against further movement for a period of time, such as time required for progress matching to be accomplished. Such constraint means can include, for example, a generated one or more duplicate stages or appliances to be successively worn by the patient. Duplicate appliances can include two or more shell appliances having the same or substantially the same geometries with respect to tooth receiving cavities. Where each appliance in a series is worn for a prescribed period of time, generating duplicate appliances can be administered to the patient and coordinated with progress tracking steps. In this manner, time for progress tracking can be afforded and more seamlessly integrated with treatment, with minimal disruption to the patient. Such constraint means or duplicate stages further prevent tooth movement relapse or movement of the teeth while an on-track/off-track assessment is being made. The creation of duplicate stages, however, should be synchronized with downstream actions planned to coincide with a particular treatment stage, such as planned tooth modification, treatment planning, and the like (e.g., interproximal reduction, dentition/appliance modeling, digital representations, etc.).

As discussed, an off-track assessment may prompt creation of the revised treatment plan. Revised treatment planning can include restaging involving manipulation of existing segmented digital models of the patient's teeth, e.g., so as to reflect current positions and shapes. The use of the existing segmented digital models advantageously avoids the added effort and expense associated with segmenting the newly acquired progress scan data. Before the newly acquired progress scan data is used to restage the planned treatment, however, it may be necessary to reset the spatial orientation between the upper and lower jaws. Resetting of the spatial orientation may be necessary where the upper and lower jaws in the newly acquired progress scan data are in different coordinate systems than were used for the existing segmented digital models of the patient's teeth. This resetting can be accomplished by retaining the matched overlay positions obtained during the previous teeth matching process, and using these retained positions to orient the jaws (see above). Matching teeth/jaw in a new coordinate system can be used for modification/generation of visualizations or graphical views of the teeth/jaws to be provided to a user (e.g., treating professional, technician, etc.). In the absence of such modifications, visual differences may be noticeable to a user. Modification with a new coordinate system can be accomplished such that visual differences in views presented to a viewer are less noticeable and revised treatment planning is more seamlessly presented to the user.

Data generated from progress tracking can optionally be utilized for revision or updating of a gingival margin or line in existing model(s). In one embodiment, the gingival line is updated based upon the current positions of the teeth by overlaying the current positions of the teeth with existing segmented models. An updated gingival line can be used to determine the cut line of a shell appliance, which can be based on the gingival/tooth margin.

The newly acquired progress scan data can also be used to set stages, e.g., initial, final positions, for the teeth that used during treatment plan revision or restaging process. For example, the current tooth positions obtained as a result of the progress tracking scan can be used as the initial tooth positions. Determination of the final tooth positions used during the restaging process can be made in at several ways. In one approach, the final tooth positions are set to be the same as the final tooth positions of the previous treatment plan, which may be rendered obsolete following off-track determination. Another approach can be used to set some of the final tooth positions equal to their respective current positions as indicated by the progress scan, and setting the positions of the other teeth to be the same as the previous final positions discussed above. This later approach may be selected in the case of individual teeth, such as molars, that were not targeted for repositioning in the previous treatment plan, but did experience some unplanned movement. Such unplanned movement may occur as a result of the movement of other teeth in the dental arch. In the event of such unplanned movement, it may be that the current positions of such teeth are acceptable, or even preferred, so that there is not any real benefit to attempt to move these teeth from their current positions.

Segmented digital models used in the restaging processes can be updated to more accurately reflect the patient's current teeth where new data is obtained in progress tracking steps. Updating may include, e.g., accounting for changes in the external shape of the patient's teeth that occurred during the prior course of treatment. For example, in some instances treatment may include removal of a portion or exterior profile of one or more of a patient's teeth, such as interproximal reduction (IPR), so as to allow sufficient clearance for the movement of the teeth during the course of orthodontic treatment. Besides IPR, there may be other changes that have been made to the patient's teeth (e.g., removed tooth, dental filling, crown, and the like) subsequent to when initial patient scan or data was obtained and used to produce an initial treatment plan, including segmented model(s) of the patient's teeth, but prior to when the progress scan data was obtained. As such, there may be differences that exist between the exterior shapes of teeth in the original data as compared to the progress scan data. Accordingly, previously existing or initial data such as tooth shape in an exisiting segmented model can be modified so as to reflect detected changes. In the case of IPR, the previously obtained tooth exterior shape can be virtually trimmed to account for the actual trimming that occurred prior to the progress scan.

Data obtained from progress tracking steps can further be utilized in assessing why the case went off track. One way of using the data involves providing or generating a visualization in which the planned positions and the current positions are shown for comparison. In one embodiment, a visualization can display the planned positions sequentially relative to the currently measured positions. Such a visualization can provide information to a viewer (e.g., technician, practitioner, etc.) for determination as to why off-track teeth have deviated from their planned repositioning, and can provide some perspective as to the relative magnitude of the off-track positional deviations. The formulation of the revised treatment plan can then be accomplished with increased insight into the reasons behind such deviations. Where a revised treatment plan is generated including restaging, a determination can be made as to the number of appliances to include in the next series/batch for delivery to the practitioner or patient.

Progress tracking steps and/or revised treatment planning will typically require data management tasks or management of newly acquired and/or existing data. In some instances, tasks can include discarding data that is no longer relevant, such as data regarding previously planned staging superceded by the revised staging, or treatment file notes that are no longer applicable. During restaging for revised treatment planning, current teeth positions can be reset to an initial or starting position, and a plurality of planned tooth positions generated for teeth moving along a revised treatment path and toward a desired position. In some instances, at least a portion of the previously existing data is retained, e.g., retained target position(s), data useful for determination/visualization of off-track progression and/or causes, and the like.

In some instances, revised treatment planning may contemplate or prescribe tooth modifications, such as use of tooth attachments during treatment. Where revised treatment planning includes use of new attachments, down-stream applications and users can be notified that a new attachment is required. Templates for positioning attachments on a patient's teeth can be built into treatment planning and scheduled for production and/or delivery to a treating professional. Where revised treatment plan requires the removal of an attachment, the treating professional can be notified (e.g., inclusion in appointment planning) that removal of the attachment is required.

As noted, methods can include synchronizing newly acquired data or information, or aspects of revised treatment, with previously planned treatment so as to integrate revisions with expectations of the treating professional and/or patient. Incorporation of progress scan data and synchronization of revised treatment, for example, can include selecting an appliance order of use indicia (e.g., numbers, colors, symbols, arrangement, etc.) matching an indicia used previously in treatment, e.g., prior to a progress tracking step.

For example, appliances may include numeric indicia designating order of use. Appliances generated according to a revised treatment plan or subsequent to a progress tracking step can be numbered to follow the indicia expected to follow in sequence the last numbered appliance provided. In such a manner, treatment revision can be accomplished in a more seamless manner from the perspective of a patient and/or treating provisional and avoid potential confusion as to prescribed appliance sequence.

Figure 13:
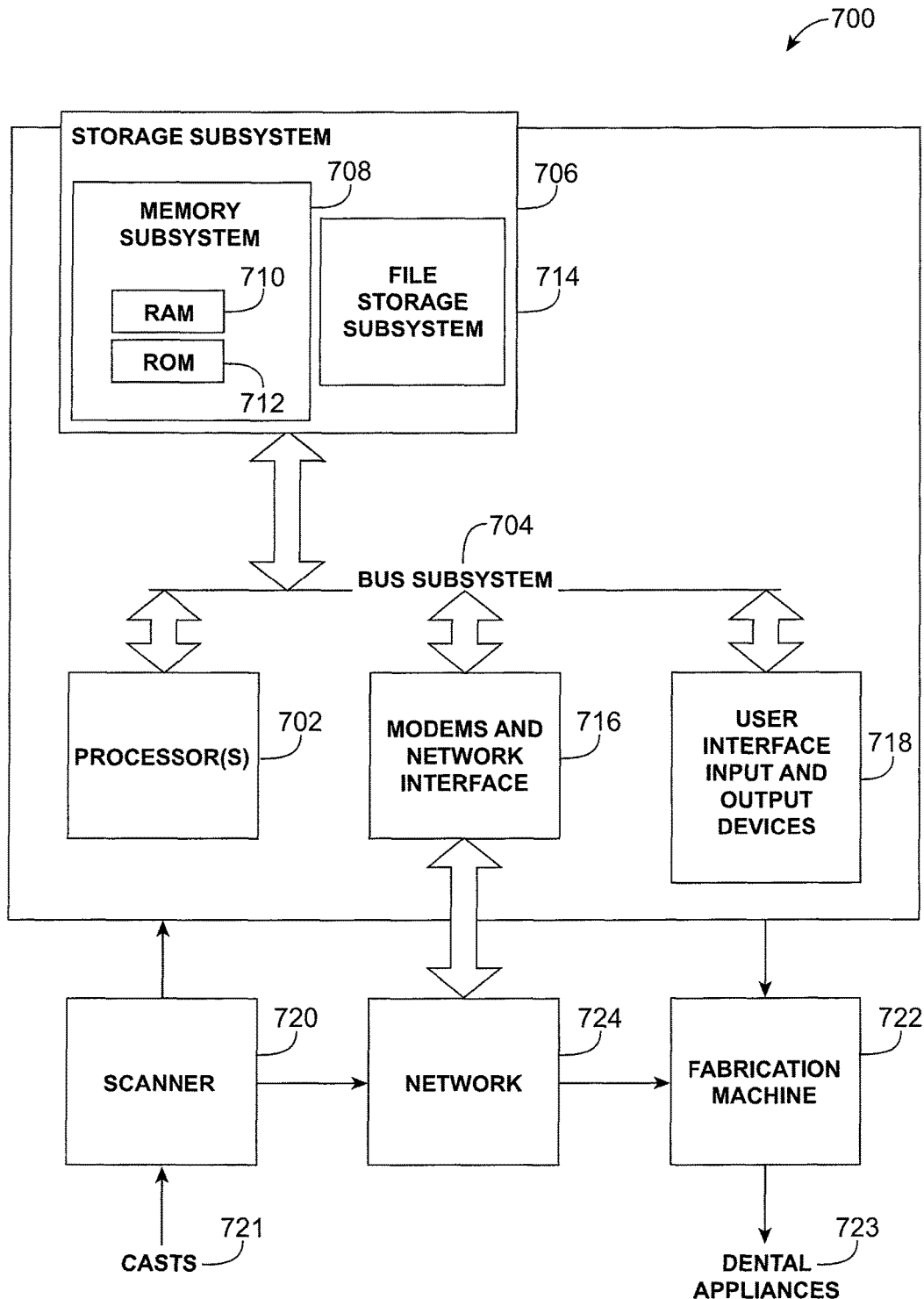
FIG. 13 is a block diagram illustrating a system for generating appliances in accordance with methods and processes of the present invention.

FIG. 13 is a simplified block diagram of a data processing system 700 that may be used in executing methods and processes described herein. The data processing system 700 typically includes at least one processor 702 that communicates with a number of peripheral devices via bus subsystem 704. These peripheral devices typically include a storage subsystem 706 (memory subsystem 708 and file storage subsystem 714), a set of user interface input and output devices 718, and an interface to outside networks 716, including the public switched telephone network. This interface is shown schematically as "Modems and Network Interface" block 716, and is coupled to corresponding interface devices in other data processing systems via communication network interface 724. Data processing system 700 can include, for example, one or more computers, such as a personal computer, workstation, mainframe, and the like.

The user interface input devices 718 are not limited to any particular device, and can typically include, for example, a keyboard, pointing device, mouse, scanner, interactive displays, etc. Similarly, various user interface output devices can be employed in a system of the invention, and can include, for example, one or more of a printer, display (e.g., visual, non-visual) system/subsystem, controller, projection device, audio output, and the like.

Storage subsystem 706 maintains the basic required programming, including computer readable media having instructions (e.g., operating instructions, etc.), and data constructs. The program modules discussed herein are typically stored in storage subsystem 706. Storage subsystem 706 typically comprises memory subsystem 708 and file storage subsystem 714. Memory subsystem 708 typically includes a number of memories (e.g., RAM 710, ROM 712, etc.) including computer readable memory for storage of fixed instructions, instructions and data during program execution, basic input/output system, etc. File storage subsystem 714 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the Internet's World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 720 includes any means for obtaining an image of a patient's teeth (e.g., from casts 721), some of which have been described herein above, which can be obtained either from the patient or from treating professional, such as an orthodontist, and includes means of providing the image data/information to data processing system 700 for further processing. In some embodiments, scanner 720 may be located at a location remote with respect to other components of the system and can communicate image data and/or information to data processing system 700, for example, via a network interface 724. Fabrication system 722 fabricates dental appliances 723 based on a treatment plan, including data set information received from data processing system 700. Fabrication machine 722 can, for example, be located at a remote location and receive data set information from data processing system 700 via network interface 724.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A method of managing delivery of an orthodontic treatment plan, comprising:
    generating a treatment plan for a patient using a computer processor, the plan comprising a plurality of digital models of successive tooth arrangements for moving teeth along a treatment path from an initial arrangement toward a selected final arrangement, the treatment plan further comprising a scheduled treatment-progress tracking event timed to correspond to the patient wearing at least one retention appliance and embodied in a tangible medium;
    providing a set of orthodontic shell appliances to the patient, the set of orthodontic shell appliances shaped based on the plurality of digital models of successive tooth arrangements and including the at least one retention appliance, the at least one retention appliance being a duplicate orthodontic shell appliance having the same geometries with respect to tooth receiving cavities as another appliance of the set of orthodontic shell appliances;
    tracking progression of the patient's teeth along the treatment path after administration of the set of orthodontic shell appliances to the patient, the tracking comprising comparing a digital model of a current arrangement of the patient's teeth to a digital model of a planned arrangement of the teeth, wherein the tracking is timed to correspond to the patient wearing the at least one retention appliance according to the treatment plan;
    generating a revised treatment plan where it is determined that treatment has progressed substantially off-track.

2. The method of claim 1, wherein the at least one retention appliance comprises a plurality of duplicate shell appliances successively worn by the patient.

3. The method of claim 1, wherein the treatment plan is based on an initial model of the patient's teeth generated prior to starting the treatment plan.

4. The method of claim 1, wherein the revised treatment plan comprises a plurality of successive tooth arrangements to move the teeth along a revised treatment path from the current arrangement directly toward the selected final arrangement.

5. The method of claim 1, further comprising setting an orientation of upper and lower jaws of the digital model of the current arrangement to substantially match a coordinate system of a previously segmented model.

6. The method of claim 1, wherein generating the revised treatment plan comprises revising at least a portion of a gingival margin in a previously segmented model based on data from the digital model of the current arrangement.

7. The method of claim 1, wherein generating the revised treatment plan comprises revising a tooth shape in a previously segmented model based on data from the digital model of the current arrangement.

8. The method of claim 7, wherein the revised tooth shape represents an inter-proximal region reduction to the patient's teeth.

9. The method of claim 1, further comprising comparing the digital model of the current arrangement to one or more previously segmented models so as to assess a cause for an off-track progression.

10. The method of claim 1, further comprising synchronizing one or more aspects of the revised treatment plan so as to integrate revised treatment with an expectation of a treating professional or patient.

11. The method of claim 10, wherein the synchronizing comprises selecting indicia designating order of use of prescribed appliances according to the revised treatment plan to sequentially follow appliances previously provided to the patient.

12. A method of managing orthodontic treatment of a patient, comprising:
generating a treatment plan for a patient using a computer processor, the plan comprising a plurality of digital models of successive tooth arrangements for moving teeth along a treatment path from an initial arrangement toward a selected final arrangement, the treatment plan further comprising a scheduled treatment-progress tracking event timed to correspond to the patient wearing at least one retention appliance;
providing a set of orthodontic shell appliances to the patient, the set of orthodontic shell appliances shaped based on the plurality of digital models of successive tooth arrangements and including the at least one retention appliance, the at least one retention appliance being a duplicate orthodontic shell appliance having the same geometries with respect to tooth receiving cavities as another appliance of the set of orthodontic shell appliances;
tracking progression of the patient's teeth along the treatment path after administration of the set of orthodontic shell appliances, the tracking comprising comparing a current arrangement of the patient's teeth to a planned arrangement of the teeth;
generating a revised treatment plan where it is determined that treatment has progressed substantially off-track, the revised treatment plan comprising one or more digital models of successive tooth arrangements for moving teeth along a second treatment path; and
synchronizing at least one aspect of the revised treatment plan so as to integrate revised treatment with an expectation of a treating professional or the patient.

13. A method of providing orthodontic treatment to a patient, comprising:
generating an orthodontic treatment plan for a patient using a computer processor, the plan comprising a plurality of digital models of successive tooth arrangements for moving teeth along a treatment path from an initial arrangement toward a selected final arrangement, the treatment plan further comprising a scheduled treatment-progress tracking event timed to correspond to the patient wearing at least one retention appliance;
providing a set of shell appliances based on the treatment plan, a first subset of the set of shell appliances shaped such that when successively worn by the patient in a designated sequence progressively move the patient's teeth at least partially along the treatment path and a second subset of the set of shell appliances including the at least one retention appliance, the at least one retention appliance being a duplicate appliance having the same geometries with respect to tooth receiving cavities as another appliance of the set of shell appliances;
receiving a representation of a current arrangement of the patient's teeth following administration of the set of shell appliances and prior to completion of the orthodontic treatment plan;
tracking progression of the patient's teeth along the treatment path after administration of the set of shell appliances, the tracking comprising comparing a current arrangement of the patient's teeth to a planned arrangement of the teeth by matching teeth from a previously segmented digital model to a surface of an unsegmented digital representation of the current arrangement and calculating one or more positional differences between the current and planned arrangements of at least some of the corresponding digital teeth;
generating a revised treatment plan where it is determined that treatment has progressed substantially off-track, the revised treatment plan comprising one or more digital models of successive tooth arrangements for moving teeth along a second treatment path; and
synchronizing at least one aspect of the revised treatment plan so as to integrate revised treatment with an expectation of a treating professional or the patient.

* * * * *